(12) United States Patent
Kanayama et al.

(10) Patent No.: US 9,376,449 B2
(45) Date of Patent: Jun. 28, 2016

(54) INDOLE CARBOXAMIDE DERIVATIVE

(71) Applicant: Astellas Pharma Inc., Chuo-ku, Tokyo (JP)

(72) Inventors: Takatoshi Kanayama, Tokyo (JP); Hideki Kubota, Tokyo (JP); Shunichiro Matsumoto, Tokyo (JP); Tomoyuki Saito, Tokyo (JP); Takafumi Shimizu, Tokyo (JP); Naoto Katoh, Tokyo (JP); Shigeo Matsui, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/413,746

(22) PCT Filed: Jul. 9, 2013

(86) PCT No.: PCT/JP2013/068780
§ 371 (c)(1),
(2) Date: Jan. 9, 2015

(87) PCT Pub. No.: WO2014/010602
PCT Pub. Date: Jan. 16, 2014

(65) Prior Publication Data
US 2015/0203505 A1    Jul. 23, 2015

(30) Foreign Application Priority Data
Jul. 10, 2012  (JP) .................. 2012-154322

(51) Int. Cl.
| | | |
|---|---|---|
| C07D 471/02 | (2006.01) | |
| A61K 31/44 | (2006.01) | |
| C07D 491/052 | (2006.01) | |
| C07D 471/04 | (2006.01) | |
| C07D 491/048 | (2006.01) | |
| C07D 209/42 | (2006.01) | |

(52) U.S. Cl.
CPC .......... *C07D 491/052* (2013.01); *C07D 209/42* (2013.01); *C07D 471/04* (2013.01); *C07D 491/048* (2013.01)

(58) Field of Classification Search
None
See application file for complete search history.

(56) References Cited

U.S. PATENT DOCUMENTS

| 5,194,614 A | 3/1993 | Andrieux et al. |
| 6,004,991 A | 12/1999 | Fourtillan et al. |
| 8,003,682 B2 | 8/2011 | Marchand et al. |

FOREIGN PATENT DOCUMENTS

| EP | 0447285 | 9/1991 |
| WO | WO 9706140 | 2/1997 |
| WO | WO 9732871 | 9/1997 |
| WO | WO 9825606 | 6/1998 |
| WO | WO 2008049996 | 5/2008 |
| WO | 2010012789 A1 | 2/2010 |

OTHER PUBLICATIONS

Blue et al., "Pharmacological Characteristics of Ro 115-1240, a Selective $\alpha_{1A/1L}$—Adrenoceptor Partial Agonist: A Potential Therapy for Stress Urinary Incontinence," BJU International, vol. 93, (2004), pp. 162-170.
Cannon et al., "Innovations in Pharmacotherapy for Stress Urinary Incontinence," Int Urogynecol J., vol. 14, (2003), pp. 367-372.
Ebisawa et al., "Expression Cloning of a High-Affinity Melatonin Receptor from *Xenopus* Dermal Melanophores," Proc. Natl. Acad. Sci. USA, vol. 91, (1994), pp. 6133-6137.
Gomez-Pinilla et al., "Effect of Melatonin on Age Associated Changes in Guinea Pig Bladder Function," The Journal of Urology, vol. 177, No. 4, (2007), pp. 1558-1561.
Hunskaar et al., "Epidemiology and Natural History of Urinary Incontinence," Int Urogynecol J., vol. 11, (2000), pp. 301-319.
International Preliminary Report on Patentability, issued in PCT/JP2013/068780, dated Jan. 22, 2015.
International Search Report, issued in PCT/JP2013/068780, dated Sep. 3, 2013.
Kaiho et al., "Role of Noradrenergic Pathways in Sneeze-Induced Urethral Continence Reflex in Rats," Am J Physiol Renal Physiol, vol. 292, (2007), pp. F639-F646.
Kato et al., "Neurochemical Properties of Ramelteon (TAK-375), a Selective $MT_1/MT_2$ Receptor Agonist," Neuropharmacology, vol. 48, (2005), pp. 301-310.

(Continued)

*Primary Examiner* — Heidi Reese
(74) *Attorney, Agent, or Firm* — Brinks Gilson & Lione

(57) ABSTRACT

The present invention relates to indole carboxamide compounds of formula (I) or a salt thereof

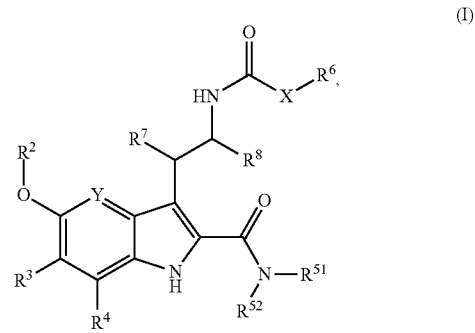

(I)

wherein $R^2$, $R^3$, $R^4$, $R^6$, $R^7$, $R^8$, $R^{51}$ and $R^{52}$ have the meanings as indicated herein, and are MT1 and/or MT2 receptor agonists useful for treating and/or preventing urological diseases.

21 Claims, No Drawings

(56) References Cited

OTHER PUBLICATIONS

Markl et al., "Synthesis and Pharmacological Evaluation of 1,2,3,4-Tetrahydropyrazino[1,2-a]indole and 2-[(phenylmethylamino)methyl]-1H-indole Analogues as Novel Melatoninergic Ligands," Bioorganic & Medicinal Chemistry, vol. 17, No. 13, (2009), pp. 4583-4594.

Miyamoto et al., "Behavioral Pharmacology of Ramelteon (TAK-375) in Small Mammals," Annals of Neurology, vol. 54, Suppl 7, (2003), p. S46.

Sarkar and Ritch, "Management of Urinary Incontinence," Journal of Clinical Pharmacy and Therapeutics, vol. 25, (2000), pp. 251-263.

Schuessler and Baessler, "Pharmacologic Treatment of Stress Urinary Incontinence: Expectations for Outcome," Urology, vol. 62, Suppl 4A, (2003), pp. 31-38.

Viktrup, "The Risk of Lower Urinary Tract Symptoms Five Years After the First Delivery," Neurology and Urodynamics, vol. 21, (2002), pp. 2-29.

von Gall et al., "Mammalian Melatonin Receptors: Molecular Biology and Signal Transduction," Cell Tissue Res., vol. 309, (200), pp. 151-162.

Zlotos et al., "2-[(2,3-Dihydro-1H-indol-1-yl)methyl]melatonin Analogues: A Novel Class of $MT_2$-Selective Melatonin Receptor Antagonists," J. Med. Chem., vol. 52, No. 3, (2009), pp. 826-833.

Office Action dated Aug. 17, 2015 for Eurasian Application No. 201590185.

Supplementary European Search Report dated Oct. 27, 2015 for EP Application No. 13816547.7.

INDOLE CARBOXAMIDE DERIVATIVE

TECHNICAL FIELD

The present invention relates to an indole carboxamide derivative which is useful as an active ingredient for a pharmaceutical composition, for example, a pharmaceutical composition for treating stress urinary incontinence.

BACKGROUND ART

Urinary incontinence is a condition in which involuntary leakage of urine is involved and recognized objectively and these become social or hygienic problems (Non-Patent Document 1). As typical examples of the urinary incontinence, urge urinary incontinence, stress urinary incontinence, and a mixed type of urinary incontinence which involves them have been known.

The most common type of the urinary incontinence is stress urinary incontinence and it has been reported that 50% of women suffering from the urinary incontinence is stress urinary incontinence (Non-Patent Document 2). The stress urinary incontinence refers to a disease in which when abdominal pressure rises during coughing, sneezing, exercise, or the like, urine leaks out involuntarily even though there is no contraction of the bladder. The causes of stress urinary incontinence can be largely divided into two types. One is the bladder neck/urethra hypermobility, in which the transmission of abdominal pressure to the urethra fails due to bladder neck ptosis, based on the pelvic floor muscle relaxation, and thus only the intravesical pressure rises during the rise of abdominal pressure and urine leaks. The other is that the reduction of a sphincter muscle function due to intrinsic sphincter deficiency causes urine leakage when the abdominal pressure rises. There is a high possibility that the onset of stress urinary incontinence involves weakening of the pelvic floor muscles due to aging and childbirth, and deterioration of the urethral function. In particular, the trauma of the pelvis by pregnancy and vaginal childbirth is known as a risk factor for a persistent stress urinary incontinence onset, and it has been reported that a prevalence rate of stress urinary incontinence for five years after the first birth is about 30% (Non-Patent Document 3).

Urge urinary incontinence is a disease in which urine leaks involuntarily immediately after a complaint of a strong suddenly occurring and irrepressible desire to urinate which is hard to endure (urge and sudden desire of urination). The mixed type of urinary incontinence is a condition in which a combination of plural types of urinary incontinence is developed, and most of them involves development of urge urinary incontinence and stress urinary incontinence.

Urinary incontinence has a major impact on the quality of life (QOL). Concerns about its symptoms restrict the range of activities of patients, making the patients feel loneliness and social isolation.

As a therapeutic drug for stress urinary incontinence, duloxetine having a serotonin-norepinephrine reuptake inhibitory action (SNRI) and nisoxetine having a selective norepinephrine reuptake inhibitory action (NRI) have been reported (Non-Patent Documents 4 and 5).

However, duloxetine has been reported to be effective against stress urinary incontinence in clinical trials, but has also been reported to have side effects such as nausea, insomnia, dizziness, and suicidal tendencies.

In the neuroreflex of the autonomic nerves by stretch stimulus of the bladder in the urine storage phase, an $\alpha_1$ adrenoceptor is present in the urethra and plays a role to maintain continence by inducing urethral contraction. To date, it has been reported that a plurality of drugs having $\alpha_1$ adrenoceptor agonistic actions have a strong urethral contraction action, and in clinical trials, a drug having an $\alpha_1$ adrenoceptor agonistic action is effective against stress urinary incontinence (Non-Patent Documents 1, 4, 6, and 7). However, it has been known that an $\alpha_1$ adrenoceptor agonist has cardiovascular side effects such as increased blood pressure or the like.

As described above, it is considered that as a drug treatment for stress urinary incontinence, it is effective to increase the urethral resistance so as to maintain continence when the intravesical pressure rises during the urine storage phase, and thus, drugs based on some mechanisms of action have been studied. However, there is a strong desire for development of an agent for treating stress urinary incontinence, based on a novel mechanism of action with fewer side effects.

Meanwhile, melatonin represented by the following formula is a hormone secreted by the pineal, which shows an inhibitory effect on the function and growth of gonad. Melatonin affects the circadian rhythm in animals, and plays a role to tune the reproductive function to a light cycle of the environment.

[Chem. 1]

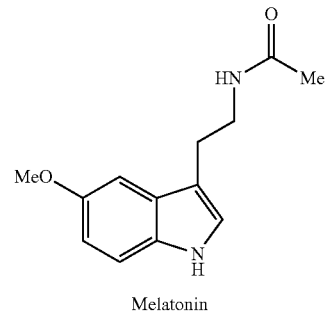

Melatonin

As the receptors of melatonin, there have been known three subtypes, MT1(Mel1a), MT2(Mel1b), and MT3(Mel1c) (Non-Patent Documents 8 and 9). MT1 and MT2 are G protein-coupled receptors (GPCR) which are coupled to Gi and Gq, but MT3 is a quinone reductase (QR2) which has a melatonin binding site. The affinity of melatonin for the MT1 and MT2 receptors is high, but the affinity of melatonin for the MT3 receptor is low (Non-Patent Document 9).

Incidentally, there have been a number of reports that MT1 and/or MT2 receptor agonists are useful for the treatment of central nervous system diseases such as sleep disorders and depression.

As the representative MT1 and/or MT2 receptor agonists, a compound represented by the following formula (A) has an MT1 and MT2 receptor agonistic activity and can be used for prevention or treatment of sleep-awake rhythm disorders, jet lag, abnormality of physical condition due to work in three shifts or the like, seasonal depression disease, reproductive and neuroendocrine diseases, senile dementia, Alzheimer's disease, various disorder due to aging, cerebral circulatory disorder, head injury, spinal cord injury, stress, epilepsy, convulsions, anxiety, depression, Parkinson's disease, hypertension, glaucoma, cancer, insomnia, diabetes mellitus, and the like. The compound has been reported to be useful for modulating immunomodulation, intelligence, tranquilizers, and ovulation control (Patent Document 1). In particular, Ramelteon represented by the following formula has been known as an agent for treating insomnia characterized by hypnagogic disorder (Non-Patent Documents 10 and 11).

[Chem. 2]

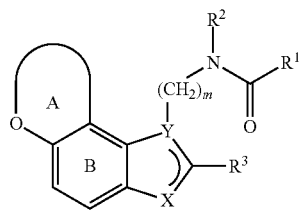

(A)

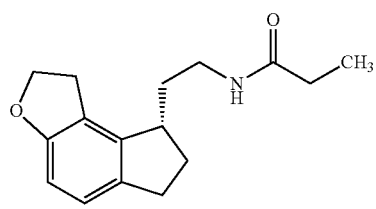

Ramelteon (Refer to this publication for the symbols in the formula.)

Moreover, it has been described that a compound represented by the following formula (B) has an MT1 and MT2 receptor agonistic activity, has many effects on the central nervous system, has particularly properties of calming, solving anxiety, antipsychotic, and analgesic, and is further useful in treatment of stress, dyssomnia, anxiety, seasonal depression, insomnia and fatigue due to jet lag, schizophrenia, panic attacks, depression, appetite adjustment, insomnia, psychotic symptoms, epilepsy, Parkinson's disease, senile dementia, and various disorders caused by common or pathological aging, migraine, memory loss, Alzheimer's disease, and blood circulation in the brain (Patent Document 2).

[Chem. 3]

(B)

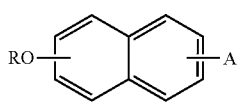

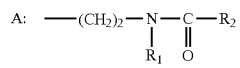

(Refer to this publication for the symbols in the formula.)

Furthermore, it has been described that a compound represented by the following formula (C) has an affinity for a melatonin receptor and is useful for the treatment of sleep disorders, periodic depression, deflection of a circadian cycle, melancholia, stress, appetite adjustment, benign prostatic hyperplasia, and the relevant conditions (Patent Document 3).

[Chem. 4]

(C)

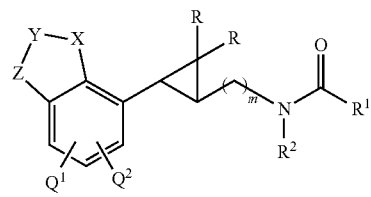

(Refer to this publication for the symbols in the formula.)

In addition, it has been described that a compound of the following formula (D) has an affinity for MT1 and MT2 receptors, is useful for treatment of stress, sleep disorders, anxiety, seasonal affective disorder or major depression, cardiovascular pathology, digestive system pathology, insomnia and fatigue due to jet lag, schizophrenia, panic attacks, depression, appetite disorders, obesity, insomnia, mental disorders, epilepsy, diabetes mellitus, Parkinson's disease, senile dementia, various disorders caused by normal or pathological aging, migraine, memory loss, and Alzheimer's disease, is useful against cerebral circulation disorders, has anovulation and immunomodulatory characteristics, and can be used for the treatment of cancer (Patent Document 4).

[Chem. 5]

(D)

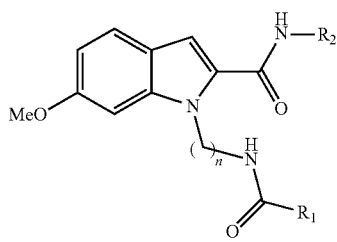

(Refer to this publication for the symbols in the formula.)

In addition, it has been described that a compound represented by the following formula (E) can be used for treatment of stress, anxiety, depression, insomnia, schizophrenia, psychosis, and epilepsy, treatment of sleep disorder associated with traveling (jet lag), and diseases due to neural degeneration (modification) of the central nervous system, such as Parkinson's disease, Alzheimer's disease or the like, and treatment of cancer, and can be used in contraception drugs or analgesics. Further, it has been described that the compound of Example 2 represented by the following formula has a superior excellent sleep effect to melatonin (Patent Document 5).

[Chem. 6]

(E)

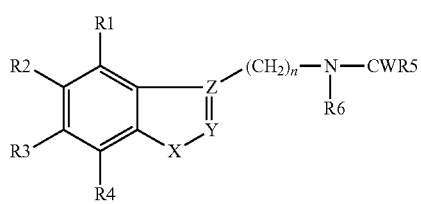

Example 2

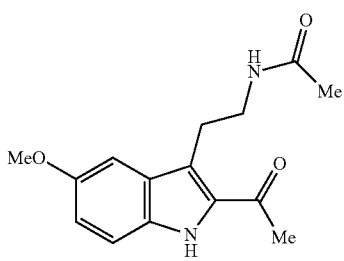 [SMILES: COc1ccc2[nH]c(C(=O)O)c(CCNC(C)=O)c2c1]

(In the formula, R1 to R6 represent a hydrogen atom, CV-R11, or lower alkylamino or the like; V represents an oxygen atom or the like; R11 represents R1; at least one of R2 and R3 represents methoxy group; R4 represents a hydrogen atom; R5 represents lower alkyl group or the like; X represents N-R7 or the like; R7 represents R1 or the like; Y represents CR8 or the like; Z represents C or the like; W represents an oxygen atom or the like; R8 represents R1; n represents integers from 1 to 4.)

Moreover, it has been described that some compounds including a compound represented by the following formula (F) have an affinity for an MT1 and/or MT2 receptor (Non-Patent Document 12).

[Chem. 7]

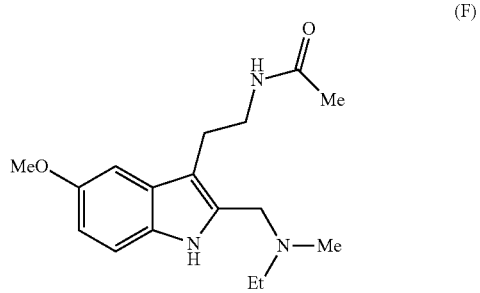

(F)

However, there is no report in any Document that MT1 and/or MT2 receptor agonists act on the urethra and are useful for the treatment of urinary incontinence and the like.

RELATED ART

Patent Document

[Patent Document 1] Pamphlet of International Publication No. WO 97/032871
[Patent Document 2] Specification of European Patent No. 447285
[Patent Document 3] Pamphlet of International Publication No. WO 98/025606
[Patent Document 4] Pamphlet of International Publication No. WO 2008/049996
[Patent Document 5] Pamphlet of International Publication No. WO 97/06140

Non-Patent Document

[Non-Patent Document 1] Journal of Clinical Pharmacy and Therapeutics, 25, 251-263 (2000)
[Non-Patent Document 2] International Urogynecology Journal, 11(5), 301-319 (2000)
[Non-Patent Document 3] Neurourology and Urodynamics, 21(1), 2-29 (2002)
[Non-Patent Document 4] International Urogynecology Journal, 14, 367-372 (2003)
[Non-Patent Document 5] American Journal of Physiology—Renal Physiology, 292(2), 639-646 (2007)
[Non-Patent Document 6] Urology, 62(Sup 4A), 31-38 (2003)
[Non-Patent Document 7] British journal of urology International, 93, 162-170 (2004)
[Non-Patent Document 8] Cell and Tissue Research, 309, 151-162 (2002)
[Non-Patent Document 9] Proceedings of the National Academy of Sciences of the United States of America, 91, 6133-6137 (1994)
[Non-Patent Document 10] Neuropharmacology, 48, 301-310 (2005)
[Non-Patent Document 11] Annals of Neurology, 54 (suppl 7), S46 (2003)
[Non-Patent Document 12] Bioorganic & Medicinal Chemistry, 17, 4583-4594 (2009)

DISCLOSURE OF INVENTION

Problems to be Solved by the Invention

The present invention provides a compound which is useful as an active ingredient for a pharmaceutical composition, for example, a pharmaceutical composition for treating urinary incontinence based on a novel mechanism of action.

Means for Solving the Problems

The present inventors found that ramelteon described above, which is a representative MT1 and/or MT2 receptor agonist, exhibits a urethra contractile action via MT1 and/or MT2 receptor, and the MT1 and/or MT2 receptor agonist is useful for the treatment of urinary incontinence. However, each of known MT1 and/or MT2 receptor agonists has an action against diseases in the central nervous system, such as sleeping disorders, depression or the like. Here, in the case where the MT1 and/or MT2 receptor agonists are used for the prevention or treatment of urinary incontinence, since it is not preferable that they exhibit an action of the diseases in the central nervous system (including, for example, a sleep action) when administered in an effective dose, it is necessary to separate the action on urinary incontinence and the action on the diseases in the central nervous system. Therefore, the present inventors have conducted extensive studies to achieve a creation of an MT1 and/or MT2 receptor agonist having a low central nervas system penetration (CNS penetration), and being expected to express an action primarily in the peripheral system; that is, a compound having an action as a peripheral MT1 and/or MT2 receptor agonist.

As a result, the present inventers have found that an indole carboxamide compound of the formula (I) has a low CNS penetration and has an peripheral and excellent MT1 and/or MT2 receptor agonistic activity, and is useful as a drug for treating urinary incontinence, thereby completing the present invention.

That is, the present invention relates to a compound of the formula (I) or a salt thereof, as well as a pharmaceutical composition comprising a compound of the formula (I) or a salt thereof and a pharmaceutically acceptable excipient.

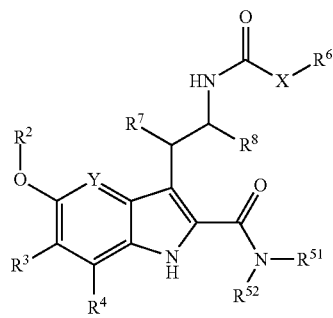

(wherein

Y is N or $CR^1$, $R^1$, $R^3$, and $R^4$ are the same as or different from each other and are each lower alkyl which may be substituted with one or more substituents selected from the group consisting of halogen, —OH, —O-lower alkyl, —O-halogeno-lower alkyl and —$NR^9R^{10}$, H, or halogen, $R^2$ is lower alkyl which may be substituted with one or more substituents selected from the group consisting of halogen and cyano, and $R^2$ may be combined with $R^1$ to form —$(CH_2)_n$—, or $R^2$ may be combined with $R^3$ to form —$(CH_2)_n$—, n is 2 or 3, $R^{51}$ and $R^{52}$ are the same as or different from each other and are each lower alkyl which may be substituted with one or more substituents selected from Group $G^2$, cycloalkyl which may be substituted with one or more substituents selected from Group $G^1$, or H, and further, $R^{51}$ and $R^{52}$ may be combined with a nitrogen atom to which they are bonded to form cyclic amino which may be substituted with one or more substituents selected from Group $G^1$, X is a bond, —$NR^{11}$—, or —$NR^{11}$—O—, $R^{11}$ is H or lower alkyl, $R^6$ is lower alkyl which may be substituted with one or more substituents selected from Group $G^4$, or cycloalkyl which may be substituted with one or more substituents selected from Group $G^3$, further, when —X—$R^6$— is —$NR^{11}$—$R^6$, $R^6$ and $R^{11}$ may be combined with a nitrogen atom to which they are bonded to form cyclic amino which may be substituted with one or more substituents selected from Group $G^3$, $R^7$ and $R^8$ are the same as or different from each other and are each lower alkyl which may be substituted with one or more substituents selected from the group consisting of halogen, —OH, and —O-halogeno-lower alkyl, or H, Group $G^1$ and Group $G^3$ include lower alkyl, halogeno-lower alkyl, halogen, —OH, —O-lower alkyl, —O-halogeno-lower alkyl, and —$NR^9R^{10}$, Group $G^2$ and Group $G^4$ include halogen, —OH, —O-lower alkyl, —O-halogeno-lower alkyl, cycloalkyl which may be substituted with one or more halogen atoms, —O-(cycloalkyl which may be substituted with one or more halogen atoms), and —$NR^9R^{10}$, and $R^9$ and $R^{10}$ are the same as or different from each other and are H or lower alkyl).

In addition, unless otherwise specified, when symbols in a certain chemical formula in the present specification are also used in another chemical formula, the same symbol represents the same meaning.

Further, the present invention relates to a pharmaceutical composition comprising the compound of the formula (I) or a salt thereof and pharmaceutically acceptable excipient thereof, in particular, a pharmaceutical composition for preventing or treating urinary incontinence. Meanwhile, the pharmaceutical composition includes an agent for preventing or treating urinary incontinence comprising the compound of the formula (I) or a salt thereof.

Furthermore, the present invention relates to use of the compound of the formula (I) or a salt thereof for the manufacture of the pharmaceutical composition for preventing or treating urinary incontinence; use of the compound of the formula (I) or a salt thereof for preventing or treating urinary incontinence; the compound of the formula (I) or a salt thereof for preventing or treating urinary incontinence; and a method for preventing or treating urinary incontinence comprising administering to a subject an effective amount of the compound of the formula (I) or a pharmaceutically acceptable salt thereof. Meanwhile, the term "subject" is a human being or another animal in need of prevention or treatment thereof, and according to a certain embodiment, a human being in need of prevention or treatment thereof.

Effects of the Invention

The compound of the formula (I) or a salt thereof is a compound which acts as a peripheral MT1 and/or MT2 receptor agonist and does not exhibits a sleep action during administration of an effective dose in the application for treatment of urinary incontinence, and therefore, it is possible to separate the action on urinary incontinence and the action on the central nervous system disease. Thus, the compound of the formula (I) or a salt thereof can be used as an active ingredient for a pharmaceutical composition for preventing and/or treating urological diseases; in one embodiment, lower urinary tract symptoms; in another embodiment, urine storage symptom, in another embodiment, urinary incontinence; in a still another embodiment, stress urinary incontinence; and the like.

EMBODIMENTS FOR CARRYING OUT THE INVENTION

Hereinafter, the present invention will be described in detail.

The "lower alkyl" refers to linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl and the like; in another embodiment, $C_{1-4}$ alkyl; in a still another embodiment, methyl; in a still further another embodiment, ethyl; and in a still further another embodiment, n-propyl.

The term "halogen" means F, Cl, Br, or I.

The "halogeno-lower alkyl" is $C_{1-6}$ alkyl substituted with one or more halogen atoms; in another embodiment, lower alkyl substituted with 1 to 5 halogen atoms; in a still another embodiment, lower alkyl substituted with 1 to 3 F atoms; in a still further another embodiment, trifluoromethyl; and in a still further another embodiment, difluoromethyl.

The "cycloalkyl" is a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl or the like; in another embodiment, $C_{3-8}$ cycloalkyl; in a still another embodiment, $C_{3-6}$ cycloalkyl; and in a still further another embodiment, cyclopropyl.

The "cyclic amino" is a group having a bonding arm on a nitrogen atom constituting a ring, among saturated or unsaturated 3- to 10-membered heterocycles which has at least one nitrogen atom as a ring-constituting atom and may have one or more hetero atoms selected from the group consisting of a nitrogen atom, an oxygen atom, and a sulfur atom, and sulfur or nitrogen which is a ring-constituting atom may be oxidized to form an oxide or a dioxide. Specific examples thereof include pyrrolidin-1-yl, piperidin-1-yl, azepan-1-yl, oxazolidin-3-yl, thiazolidin-3-yl, 1,1-dioxidothiazolidin-3-yl, isoxazolidin-2-yl, isothiazolidin-2-yl, 1,1-dioxidoisothiazolidin-2-yl, piperazin-1-yl, morpholin-4-yl, thiomorpholin-4-yl, 1,1-dioxide thiomorpholin-4-yl, indolin-1-yl, isoindolin-2-yl, 1,2,3,4-tetrahydroquinolin-1-yl, 1,2,3,4-tetrahydroisoquinolin-2-yl, decahydroquinolin-1-yl, decahydroisoquinolin-2-yl, 4,5,6,7-tetrahydrothieno[3,2-c]pyridin-5-yl and the like; and in another embodiment, pyrrolidin-1-yl, piperidin-1-yl, and morpholin-1-yl.

In the present specification, the expression "which may be substituted" represents "which is not substituted" or "which is substituted with 1 to 5 substituents". Further, if it has a plurality of substituents, the substituents may be the same as or different from each other.

Certain embodiments of the compound of the formula (I) of the present invention are shown below.

(1) The compound or a salt thereof, in which Y is N or $CR^1$; in another embodiment, the compound or a salt thereof, in which Y is $CR^1$; and in still another embodiment, the compound or a salt thereof, in which Y is N.

(2) The compound or a salt thereof, in which $R^1$ is lower alkyl which may be substituted with one or more substituents selected from the group consisting of halogen, —O-lower alkyl, and —O-halogeno-lower alkyl, H, or halogen; in another embodiment, the compound or a salt thereof, in which $R^1$ is H or halogen; in a still another embodiment, the compound or a salt thereof, in which $R^1$ is H or F; and in a still further another embodiment, the compound or a salt thereof, in which $R^1$ is H.

(3) The compound or a salt thereof, in which $R^3$ and $R^4$ are the same as or different from each other and are lower alkyl which may be substituted with one or more substituents selected from the group consisting of halogen, —O-lower alkyl, and —O-halogeno-lower alkyl, H, or halogen; in another embodiment, the compound or a salt thereof, in which $R^3$ and $R^4$ are the same as or different from each other and are lower alkyl, halogeno-lower alkyl, H, or halogen; in a still another embodiment, the compound or a salt thereof, in which $R^3$ and $R^4$ are the same as or different from each other and are H or halogen; and in a still further another embodiment, the compound or a salt thereof, in which $R^3$ and $R^4$ are the same as or different from each other and are H or F.

(4) The compound or a salt thereof, in which $R^2$ is lower alkyl which may be substituted with one or more substituents selected from the group consisting of halogen and cyano, $R^2$ may be combined with $R^1$ to form —$(CH_2)_n$—, or $R^2$ may be combined with $R^3$ to form —$(CH_2)_n$—, and n is 2 or 3; in another embodiment, the compound or a salt thereof, in which $R^2$ is lower alkyl which may be substituted with one or more substituents selected from the group consisting of halogen and cyano, $R^2$ may be combined with $R^1$ to form —$(CH_2)_2$—, or $R^2$ may be combined with $R^3$ to form —$(CH_2)_2$—; in a still another embodiment, the compound or a salt thereof, in which $R^2$ is lower alkyl or lower alkyl substituted with halogeno-lower alkyl or cyano; in a still further another embodiment, the compound or a salt thereof, in which $R^2$ is lower alkyl or halogeno-lower alkyl; in a still further another embodiment $R^2$ is lower alkyl; and in a still further another embodiment, the compound or a salt thereof, in which $R^2$ is methyl.

(5) The compound or a salt thereof, in which $R^{51}$ and $R^{52}$ are the same as or different from each other and are lower alkyl which may be substituted with one or more substituents selected from Group $G^{21}$, cycloalkyl which may be substituted with one or more substituents selected from Group $G^{11}$, or H, in which Group $G^{11}$ includes lower alkyl, halogeno-lower alkyl, halogen, —OH, or —O-lower alkyl, and Group $G^{21}$ includes halogen, —OH, —O-lower alkyl, —O-halogeno-lower alkyl, and $NR^9R^{10}$, in which $R^9$ and $R^{10}$ are the same as or different from each other and are H or lower alkyl; in another embodiment, the compound or a salt thereof, in which $R^{51}$ and $R^{52}$ are the same as or different from each other and are lower alkyl which may be substituted with one or more substituents selected from the group consisting of —OH, —O-lower alkyl, —$NH_2$, —NH(lower alkyl), and —N(lower alkyl)$_2$; cycloalkyl which may be substituted with one or more substituents selected from the group consisting of lower alkyl, —OH, and —O-lower alkyl; or H; in a still another embodiment, the compound or a salt thereof, in which $R^{51}$ and $R^{52}$ are the same as or different from each other and are lower alkyl, cycloalkyl, or H; in a still further another embodiment, the compound or a salt thereof, in which $R^{51}$ and $R^{52}$ are the same as or different from each other and are lower alkyl or H; in a still further another embodiment, the compound or a salt thereof, in which $R^{51}$ and $R^{52}$ are the same as or different from each other and are methyl or H; in a still further another embodiment, the compound or a salt thereof, in which $R^{51}$ is lower alkyl and $R^{52}$ is H; and in a still further another embodiment, the compound or a salt thereof, in which $R^{51}$ is methyl and $R^{52}$ is H.

(6) The compound or a salt thereof, in which X is a bond, —$NR^{11}$—, or —$NR^{11}$—O—, and $R^{11}$ is H or lower alkyl; in another embodiment, the compound or a salt thereof, in which X is a bond, —NH—, or —NH—O—; in a still another embodiment, X is a bond or —NH—; in a still another embodiment, X is —NH— or —NH—O—; in a still another embodiment, the compound or a salt thereof, in which X is a bond; in a still further another embodiment, the compound or a salt thereof, in which X is —NH— or —N(lower alkyl)-; in a still further another embodiment, the compound or a salt thereof, in which X is —NH—.

(7) The compound or a salt thereof, in which $R^6$ is lower alkyl which may be substituted with one or more substituents selected from Group $G^{41}$, or cycloalkyl which may be substituted with one or more substituents selected from Group $G^{31}$, in which Group $G^{31}$ includes lower alkyl, halogeno-lower alkyl, halogen, —OH, and —O-lower alkyl, and Group $G^{41}$ includes halogen, —OH, —O-lower alkyl, —O-halogeno-lower alkyl, and cycloalkyl; in another embodiment, the compound or a salt thereof, in which $R^6$ is lower alkyl which may be substituted with one or more substituents selected from the group consisting of halogen, —O-lower alkyl, and —OH; or cycloalkyl which may be substituted with one or more substituents selected from the group consisting of lower alkyl, halogeno-lower alkyl, —OH, and —O-lower alkyl; in a still another embodiment, the compound or a salt thereof, in which $R^6$ is lower alkyl which may be substituted with one or more substituents selected from the group consisting of halogen and —O-lower alkyl; or cycloalkyl which may be substituted with one or more substituents selected from lower alkyl, halogeno-lower alkyl, and —O-lower alkyl; in a still further another embodiment, the compound or a salt thereof, in which $R^6$ is lower alkyl which may be substituted with one or more substituents selected from the group consisting of halogen and —O-lower alkyl, or cycloalkyl; in a still further another embodiment, the compound or a salt thereof, in which $R^6$ is lower alkyl or halogeno-lower alkyl; in a still further another embodiment, the compound or a salt thereof, in which $R^6$ is methyl or difluoromethyl; in a still further another embodiment, the compound or a salt thereof, in which $R^6$ is lower alkyl; and in a still further another embodiment, the compound or a salt thereof, in which $R^6$ is methyl.

(8) The compound or a salt thereof, in which $R^7$ and $R^8$ are the same as or different from each other and are lower alkyl or H; in another embodiment, the compound or a salt thereof, in which $R^7$ and $R^8$ are the same as or different from each other and are methyl or H; and in a still another embodiment, the compound or a salt thereof, in which $R^7$ and $R^8$ are all H.

(9) The compound which is a combination of two or more of the groups in (1) to (8) above.

The present invention includes the compound or a salt thereof as described in (9), which is a combination of two or more of the embodiments described in (1) to (8) above, and specific examples thereof include the following embodiments.

(10) The compound or a salt thereof, in which
Y is N or $CR^1$,
$R^1$ is lower alkyl which may be substituted with one or more substituents selected from the group consisting of halogen, —O-lower alkyl, and —O-halogeno-lower alkyl, H, or halogen,
$R^3$ and $R^4$ are the same as or different from each other and are lower alkyl which may be substituted with one or more substituents selected from the group consisting of halogen, —O-lower alkyl, and —O-halogeno-lower alkyl, H, or halogen,
$R^2$ is lower alkyl which may be substituted with one or more substituents selected from the group consisting of halogen and cyano, and $R^2$ may be combined with $R^1$ to form —$(CH_2)_n$—, or $R^2$ may be combined with $R^3$ to form —$(CH_2)_n$—, and n is 2 or 3,
$R^{51}$ and $R^{52}$ are the same as or different from each other and are lower alkyl which may be substituted with one or more substituents selected from Group $G^{21}$, cycloalkyl which may be substituted with one or more substituents selected from Group $G^{11}$, or H, in which Group $G^{11}$ includes lower alkyl, halogeno-lower alkyl, halogen, —OH, and —O-lower alkyl, and Group $G^{21}$ includes halogen, —OH, —O-lower alkyl, —O-halogeno-lower alkyl, and $NR^9R^{10}$,
$R^9$ and $R^{10}$ are the same as or different from each other and are H or lower alkyl,
X is a bond, —$NR^{11}$— or —$NR^{11}$—O—, and $R^{11}$ is H or lower alkyl,
$R^6$ is lower alkyl which may be substituted with one or more substituents selected from Group $G^{41}$, or cycloalkyl which may be substituted with one or more substituents selected from Group $G^{31}$, in which Group $G^{31}$ includes lower alkyl, halogeno-lower alkyl, halogen, —OH, and —O-lower alkyl, and Group $G^{41}$ includes halogen, —OH, —O-lower alkyl, —O-halogeno-lower alkyl and cycloalkyl, and
$R^7$ and $R^8$ are the same as or different from each other and are lower alkyl or H.

(11) The compound or a salt thereof as described in (10) above, in which
$R^1$ is H or halogen,
$R^3$ and $R^4$ are the same as or different from each other and are lower alkyl, halogeno-lower alkyl, H, or halogen,
$R^{51}$ and $R^{52}$ are the same as or different from each other and are lower alkyl which may be substituted with one or more substituents selected from the group consisting of —OH, —O-lower alkyl, —$NH_2$, —NH(lower alkyl), and —N(lower alkyl)$_2$; cycloalkyl which may be substituted with one or more substituents selected from the group consisting of lower alkyl, —OH, and —O-lower alkyl; or H,
X is a bond, —NH—, or —NH—O—, and
$R^6$ is lower alkyl which may be substituted with one or more substituents selected from the group consisting of halogen, —O-lower alkyl, and —OH; or cycloalkyl which may be substituted with one or more substituents selected from the group consisting of lower alkyl, halogeno-lower alkyl, —OH, and —O-lower alkyl.

(12) The compound or a salt thereof as described in (11) above, in which
$R^2$ is lower alkyl which may be substituted with one or more substituents selected from the group consisting of halogen and cyano, and further, $R^2$ may be combined with $R^1$ to form —$(CH_2)_2$—, or $R^2$ may be combined with $R^3$ to form —$(CH_2)_2$—,
$R^3$ and $R^4$ are the same as or different from each other and are H or halogen,
$R^{51}$ and $R^{52}$ are the same as or different from each other and are lower alkyl, cycloalkyl, or H,
X is bond, —NH—, or —NH—O—, and
when X is a bond, $R^6$ is lower alkyl which may be substituted with one or more substituents selected from the group consisting of halogen and —O-lower alkyl, or cycloalkyl, or
when X is —NH— or —NH—O, $R^6$ is lower alkyl, and
$R^7$ and $R^8$ are all H.

(13) The compound or a salt thereof as described in (12) above, in which
$R^2$ is lower alkyl,
$R^{51}$ and $R^{52}$ are the same as or different from each other and are lower alkyl or H, and
when X is a bond, $R^6$ is lower alkyl or halogeno-lower alkyl, or
when X is —NH— or —NH—O—, $R^6$ is lower alkyl.

(14) The compound or a salt thereof as described in (13) above, in which
$R^1$ is H or F,
$R^2$ is methyl,
$R^3$ and $R^4$ are the same as or different from each other and are H or F,
X is a bond or —NH—, and
when X is a bond, $R^6$ is methyl or difluoromethyl, or
when X is —NH—, $R^6$ is methyl.

(15) The compound or a salt thereof as described in any one of (10) to (14) above, in which Y is $CR^1$, $R^1$ is H, and X is a bond.

(16) The compound or a salt thereof as described in any one of (10) to (14) above, in which Y is $CR^1$, $R^1$ is H, and X is —NH—.

(17) The compound or a salt thereof in any one of (10) to (14) above, in which Y is N and X is a bond.

(18) The compound or a salt thereof as described in any one of (10) to (14) above, in which Y is N and X is —NH—.

(19) The compound or a salt thereof as described in (10) above, in which
$R^3$ and $R^4$ are the same as or different from each other and are H or halogen,
$R^2$ is lower alkyl or halogeno-lower alkyl,
$R^{51}$ and $R^{52}$ are the same as or different from each other and are lower alkyl, cycloalkyl, or H, $R^6$ is lower alkyl which may be substituted with one or more substituents selected from the group consisting of halogen and —O-lower alkyl, or cycloalkyl, and
$R^7$ and $R^8$ are the same as or different from each other and are methyl or H.

(20) The compound or a salt thereof as described in (10) above, in which
$R^3$ and $R^4$ are the same as or different from each other and are H or halogen,
$R^2$ is methyl,
$R^{51}$ and $R^{52}$ are the same as or different from each other and are methyl or H, $R^6$ is lower alkyl or halogeno-lower alkyl, and
$R^7$ and $R^8$ are H.

(21) The compound or a salt thereof as described in (19) or (20) above, in which Y is $CR^1$, $R^1$ is H, and X is a bond.

(22) The compound or a salt thereof as described in (19) or (20) above, in which Y is $CR^1$, $R^1$ is H, and X is —NH—.

(23) The compound or a salt thereof as described in (19) or (20) above, in which Y is N and X is a bond.

(24) The compound or a salt thereof as described in (19) or (20) above, in which Y is N and X is —NH—.

Examples of the specific compounds included in the present invention include the following compounds:

3-(2-acetamidoethyl)-5-methoxy-N-methyl-1H-indole-2-carboxamide,

3-{2-[(difluoroacetyl)amino]ethyl}-5-methoxy-N-methyl-1H-indole-2-carboxamide,

3-{2-[(difluoroacetyl)amino]ethyl}-6-fluoro-5-methoxy-N-methyl-1H-indole-2-carboxamide, 3-(2-acetamidoethyl)-6-fluoro-5-methoxy-N-methyl-1H-indole-2-carboxamide, and 5-methoxy-N-methyl-3-{2-[(methylcarbamoyl)amino]ethyl}-1H-indole-2-carboxamide.

The compound of the formula (I) may exist in the form of tautomers or geometrical isomers depending on the kind of substituents. In the present specification, the compound of the formula (I) shall be described in only one form of isomer, yet the present invention includes other isomers, and also includes isolated forms of the isomers, or a mixture thereof.

In addition, the compound of the formula (I) may have asymmetric carbon atoms or axial chirality in some cases, and correspondingly, it may exist in the form of optical isomers. The present invention includes both an isolated form of the optical isomers of the compound of the formula (I) or a mixture thereof.

Furthermore, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, and the like.

The salts of the compound of the formula (I) can also be prepared by carrying out a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemate (for example, fractional crystallization for inducing diastereomer salts with optically active bases or acids, chromatography using a chiral column or the like, and others), and further, the isomers can also be prepared from an appropriate optically active starting compound.

In addition, the present invention also includes various hydrates or solvates, and crystal polymorph substances of the compound of the formula (I) or a salt thereof. In addition, the present invention also includes compounds labeled with various radioactive or non-radioactive isotopes.

In one embodiment, urinary incontinence is stress urinary incontinence, urge urinary incontinence, or a mixed type of urinary incontinence; in another embodiment, stress urinary incontinence or a mixed type of urinary incontinence; in a still another embodiment, stress urinary incontinence; and in a still another embodiment, a mixed type of urinary incontinence.

In the present specification, stress urinary incontinence is a disease in which when abdominal pressure rises during coughing, sneezing, exercise, or the like, urine leaks out involuntarily even though there is no contraction of the bladder. Urge urinary incontinence is a disease in which urine leaks involuntarily immediately after a complaint of a strong suddenly occurring and irrepressible desire to urinate which is hard to endure (urge and sudden desire of urination). The mixed type of urinary incontinence refers to a disease in which a combination of stress urinary incontinence and at least one urinary incontinence selected from the group consisting of urge urinary incontinence, functional urinary incontinence, reflex urinary incontinence, overflow urinary incontinence, and genuine urinary incontinence is developed. In one embodiment, the mixed type of urinary incontinence is a disease in which a combination of urge urinary incontinence and stress urinary incontinence is developed.

It has been reported that the "CNS penetration" can be expressed by an index indicating a ratio of the concentration of the test compound in the cerebrospinal fluid (which may be hereinafter described as CSF in some cases) (which may be hereinafter described as $C_{CSF}$ in some cases) to the unbound concentration of the test compound in the plasma (which may be hereinafter described as $C_{plasma,u}$ in some cases) which is the ratio of unbound concentration in the CSF-plasma (which means a value represented by $C_{CSF}/C_{plasma,u}$, and may be hereinafter described as $K_{p,uu,CSF}$ in some cases), or a ratio of the total concentration of the test compound in the brain (which may be hereinafter described as $C_{brain}$ in some cases) to the total concentration of the test compound in the plasma (which may be hereinafter described as $C_{plasma,t}$ in some cases) which is the ratio of the concentration in the brain-plasma (which means a value represented by $C_{brain}/C_{plasma,t}$, and may be hereinafter described as $K_{p,brain}$ in some cases) (Xenobiotica, 42, 11-27 (2012) and J. Pharmacol. Exp. Ther., 325, 349-356 (2008)). For example, it has been described that using, for example, a sample collected after 15 minutes from the intravenous administration of the test compound, the ratio of unbound concentration in the CSF-plasma (which may be hereinafter described as $K_{p,uu,CSF,iv15min}$ in some cases) from the drug concentrations in CSF and the plasma is calculated, from which the CNS penetration is evaluated. Further, it has been described that with plural drugs known to have a low CNS penetration, that is, Verapamil, Quinidine, and Imatinib, the $K_{p,uu,CSF}$ value was a value of 0.11 or less.

In the present invention, "peripheral" means that the CNS penetration is low, in one embodiment, the value of $K_{p,uu,CSF,iv15min}$ is 0.20 or less; in another embodiment, the value of $K_{p,uu,CSF,iv15min}$ is 0.11 or less; in a still another embodiment, the value of $K_{p,uu,CSF,iv15min}$ is 0.10 or less; in a still further another embodiment, the value of $K_{p,brain}$ is 0.20 or less, in a still further another embodiment, the value of $K_{p,brain}$ is 0.15 or less; and in a still further another embodiment, $K_{p,brain}$ is 0.10 or less.

"MT1 and/or MT2 receptor" includes, as an embodiment, MT1 receptor and MT2 receptor, and as another embodiment MT1 receptor.

The "compound having an action as a peripheral MT1 and/or MT2 receptor agonist" means a compound having a human MT1 and/or human MT2 receptor agonistic action as described later as well as low CNS penetration; and in one embodiment, a compound having an $EC_{50}$ described in Test Example 1 as described later is 100 nM or less as well as a value of $K_{p,uu,CSF}$ of 0.2 or less; in another embodiment, a compound having the $EC_{50}$ of 60 nM or less as well as a value of $K_{p,uu,CSF}$ of 0.2 or less; and in a still another embodiment, a compound having the $EC_{50}$ of 60 nM or less as well as the value of $K_{p,uu,CSF}$ of 0.11 or less.

(Preparation Methods)

The compound of the formula (I) or a salt thereof can be prepared using the characteristics based on the basic structure or the type of substituents and by applying various known synthesis methods. During the preparation, replacement of the functional group with a suitable protective group (a group that can be easily converted into the functional group) at the stage from starting material to an intermediate may be effective depending on the type of functional groups in the production technology in some cases. Such a protective group may include, for example, the protective groups described in "Greene's Protective Groups in Organic Synthesis (4$^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, or by further carrying out the reaction using the obtained compound of the formula (I), as in the case of the above-mentioned protective group. The reaction can be carried out by using methods known to those skilled in the art, such as ordinary esterification, amidation, and dehydration.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

[Chem. 9]

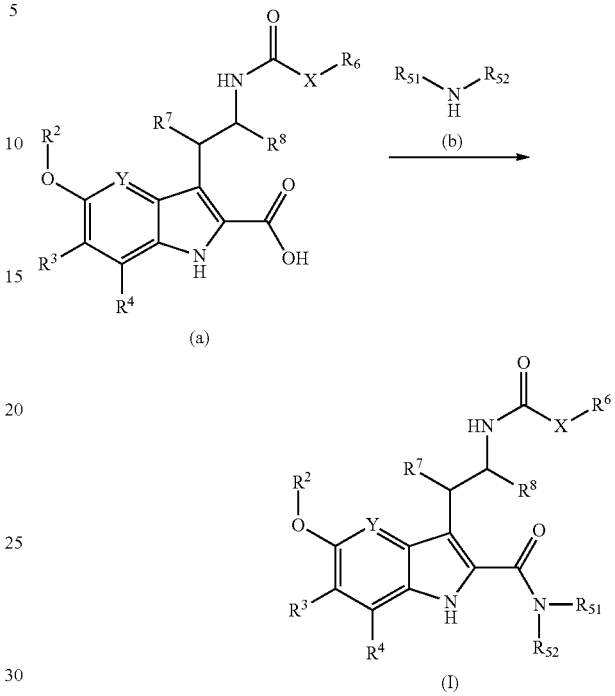

The present production process is a method for preparing the compound of the formula (I) which is the compound of the present invention by subjecting a compound (a) to amidation.

In this reaction, the compound (a) and a compound (b) in equivalent amounts, or either thereof in an excess amount are used, and the mixture is stirred in a solvent which is inert to the reaction, under from cooling to heating, and preferably from −20° C. to 60° C., usually for 0.1 hours to 5 days, in the presence of a condensing agent. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran, dioxane, dimethoxyethane and the like, N,N-dimethyl formamide, dimethyl sulfoxide, ethyl acetate, acetonitrile, water, or a mixture thereof. Examples of the condensing agent include, but are not limited to, 1-(3-dimethylaminopropyl)-3-ethylcarbodiimide, dicyclohexylcarbodiimide, 1,1'-carbonyldiimidazole, diphenylphosphoryl azide, and phosphorus oxychloride. It is preferable in some cases for the progress of the reaction to use an additive (for example, 1-hydroxybenzotriazole). In addition, it is preferable in some cases for the smooth progress of the reaction to use organic bases such as triethylamine, N,N-diisopropylethylamine, N-methylmorpholine and the like, or inorganic bases such as potassium carbonate, sodium carbonate, potassium hydroxide and the like.

Furthermore, it is also possible to use a method in which compound (a) is converted to a reactive derivative thereof, which is then reacted with a compound (b). Examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutyl chloroformate or the like, and active esters that can be obtained by condensation with 1-hydroxybenzotriazole or the like. The reaction of the reactive derivatives with the compound (b) can be carried out under from cooling to heating, and preferably from −20° C. to 60° C., in a solvent which is inert to the reaction, such as halogenated hydrocarbons, aromatic hydrocarbons, and ethers.

[References]

"Organic Functional Group Preparations" written by S. R. Sandler and W. Karo, 2$^{nd}$ edition, Vol. 1, Academic Press Inc., 1991, "Courses in Experimental Chemistry (5$^{th}$ edition)" edited by The Chemical Society of Japan, Vol. 16 (2005) (Maruzen).

(Production Process 2-1)

[Chem. 10]

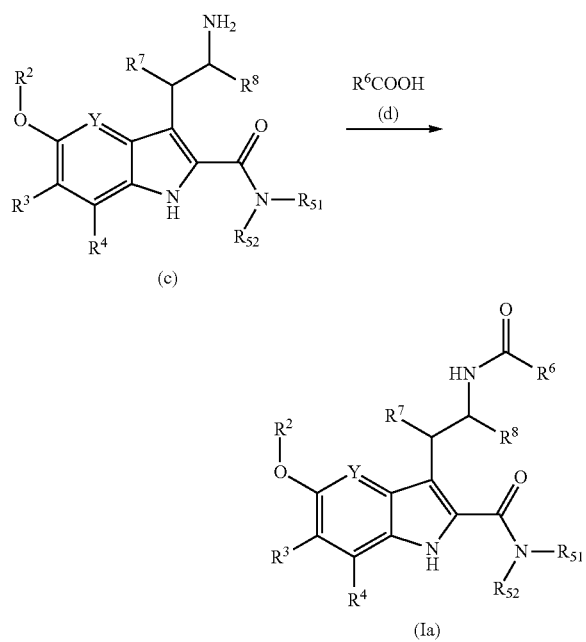

The present production process is a method in which a compound (c) and a compound (d) are used and subjected to amidation to prepare compound (Ia) which is the compound of the formula (I), in which X is a bond, as a compound of the present invention. The reaction condition is the same as that in Production Process 1.

(Production Process 2-2)

[Chem. 11]

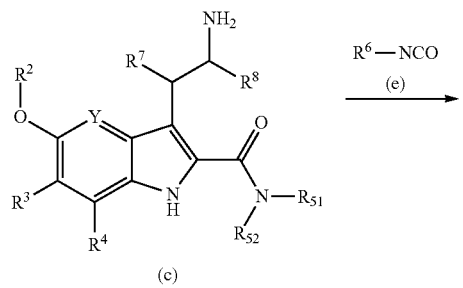

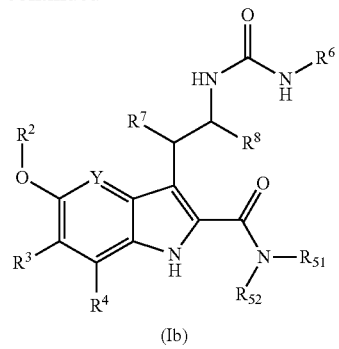

The present production process is a method in which a compound (c) and a compound (e) are used and subjected to form a urea to prepare a compound (Ib), which is the compound of the formula (I), in which X is —NH—.

In this reaction, the compound (c) and the compound (e) in equivalent amounts, or either thereof in an excess amount are used, and the mixture is stirred in a solvent which is inert to the reaction or without a solvent, under any temperature condition from cooling to heating and refluxing, and preferably from 0° C. to room temperature, usually for 0.1 hours to 5 days. Examples of the solvent used herein are not particularly limited, but include halogenated hydrocarbons such as dichloromethane, 1,2-dichloroethane, chloroform and the like, aromatic hydrocarbons such as benzene, toluene, xylene and the like, ethers such as diethyl ether, tetrahydrofuran, dioxane, dimethoxyethane and the like, N,N-dimethyl formamide, dimethyl sulfoxide, acetonitrile, and a mixture thereof.

The isocyanate (e) can be prepared by a Curtius rearrangement of the corresponding acid azide compound, a Hoffmann rearrangement of a primary amide compound, or the like. The acid azide can be prepared by reacting a carboxylic acid with an azide salt such as sodium azide and the like in the presence of an activating agent or by reacting a carboxylic acid with diphenyl phosphoryl azide.

[References]

"Organic Functional Group Preparations" written by S. R. Sandler and W. Karo, 2$^{nd}$ edition, Vol. 2, Academic Press Inc., 1991

(Production Process 2-3)

[Chem. 12]

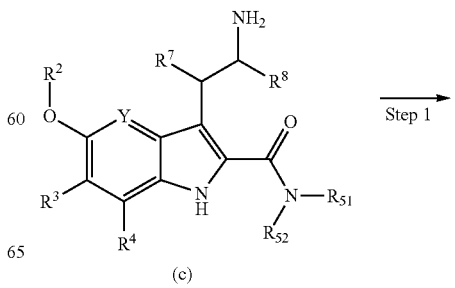

-continued

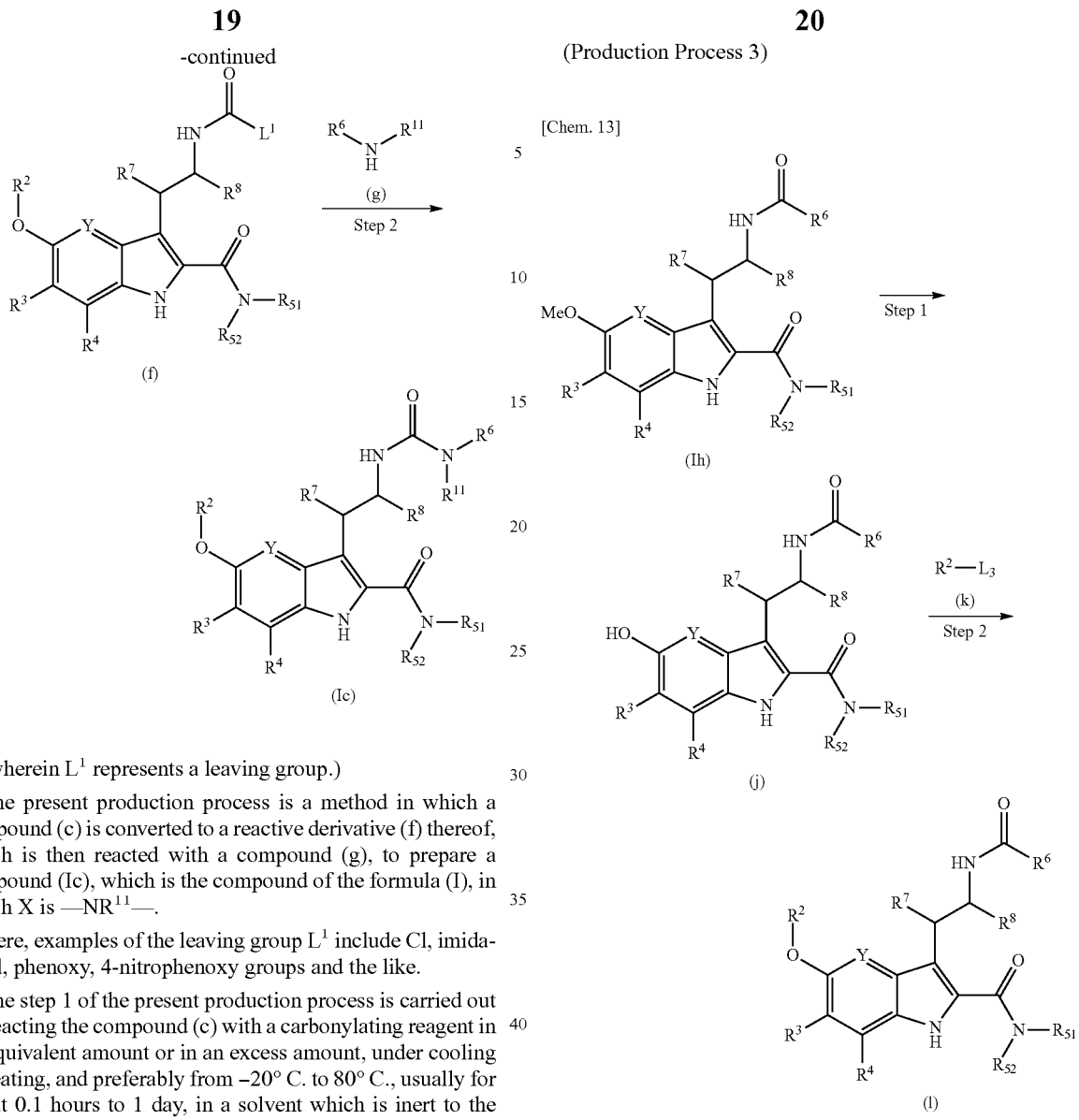

(wherein L¹ represents a leaving group.)

The present production process is a method in which a compound (c) is converted to a reactive derivative (f) thereof, which is then reacted with a compound (g), to prepare a compound (Ic), which is the compound of the formula (I), in which X is —NR¹¹—.

Here, examples of the leaving group L¹ include Cl, imidazolyl, phenoxy, 4-nitrophenoxy groups and the like.

The step 1 of the present production process is carried out by reacting the compound (c) with a carbonylating reagent in an equivalent amount or in an excess amount, under cooling to heating, and preferably from −20° C. to 80° C., usually for about 0.1 hours to 1 day, in a solvent which is inert to the reaction, in the presence of a base. In the step 2, without isolating the compound (f) which is the product of step 1, to the reaction mixture is added a compound (g) in an equivalent amount or in an excess amount, and the mixture is reacted under cooling to heating, and preferably from −20° C. to 80° C., usually for about 0.1 hours to 1 day. Examples of the solvent as used herein are not particularly limited, but include halogenated hydrocarbons such as dichloromethane, 1,2-dichloroethane, chloroform and the like, aromatic hydrocarbons such as benzene, toluene, xylene and the like, ethers such as diethyl ether, tetrahydrofuran, dioxane, dimethoxyethane and the like, N,N-dimethyl formamide, dimethyl sulfoxide, ethyl acetate, acetonitrile, and a mixture thereof. Examples of the carbonylating reagent include diphosgene, triphosgene, 1,1'-carbonyldiimidazole, 4-nitrophenyl chloroformate, phenyl chloroformate and the like. When the reactive derivative (f) which is an intermediate is stable, this may be first isolated and then the next reaction may be carried out.

[References]

"Organic Functional Group Preparations" written by S. R. Sandler and W. Karo, 2nd edition, Vol. 2, Academic Press Inc., 1991

(Production Process 3)

[Chem. 13]

(wherein $L_3$ represents a leaving group.)

The present production process is a method in which the compound of the formula (Ih), which is the compound of the formula (I), in which R² is methyl, is subjected to a demethylation reaction, to prepare the compound of the formula (I).

The step 1 of the present production process is a step of a reaction for demethylation from a methoxy group. The reaction for demethylation can be carried out with reference to "Protective Groups in Organic Synthesis" written by Greene and Wuts, 4th edition, John Wiley & Sons Inc., 2006.

The step 2 is a reaction for alkylating phenol. The compound of formula (I) can be obtained by reacting a compound (j) obtained in the step 1 with a compound (k). Here, examples of the leaving group of $L_3$ include halogen, methanesulfonyloxy, p-toluenesulfonyloxy and the like.

In this reaction, the compound (j) and the compound (k) in equivalent amounts, or either thereof in an excess amount are used, and the mixture is stirred in a solvent which is inert to the reaction, under cooling to heating and refluxing, and preferably from 0° C. to 80° C., usually for 0.1 hours to 5 days, in the presence of a base. Examples of the solvent used herein are not particularly limited, but include aromatic hydrocarbons such as benzene, toluene, xylene and the like, ethers such as diethyl ether, tetrahydrofuran, dioxane, dimethoxyethane and the like, halogenated hydrocarbons such as dichloromethane, 1,2-dichloroethane, chloroform and the like, N,N-dimethyl formamide, dimethyl sulfoxide, ethyl acetate, acetonitrile, and a mixture thereof. Examples of the base include organic bases such as triethylamine, diisopropylethylamine, 1,8-diazabicyclo[5.4.0]-7-undecene, n-butyllithium and the like, and inorganic bases such as sodium carbonate, potassium carbonate, sodium hydride, potassium tert-butoxide and the like. It may be advantageous to carry out a reaction in the presence of a phase transfer catalyst such as tetra-n-butylammonium chloride and the like in some cases.

[References]

"Organic Functional Group Preparations" written by S. R. Sandler and W. Karo, $2^{nd}$ edition, Vol. 1, Academic Press Inc., 1991

"Courses in Experimental Chemistry" ($5^{th}$ edition) edited by The Chemical Society of Japan, Vol. 14 (2005) (Maruzen)

(Preparation of Starting Compound)

In the preparation methods above, the starting compound can be prepared by using any of, for example, the methods below, the methods described in Preparation Examples as described later, known methods, or modified methods thereof.

(Starting Material Synthesis 1)

[Chem. 14]

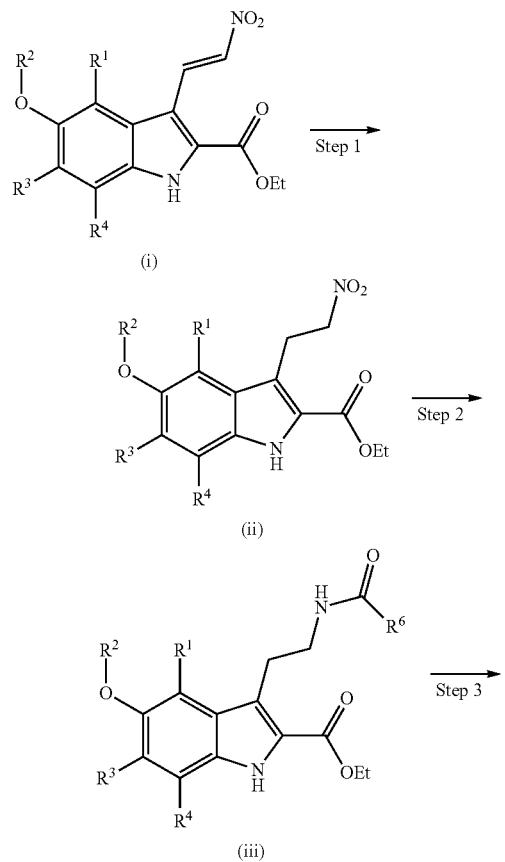

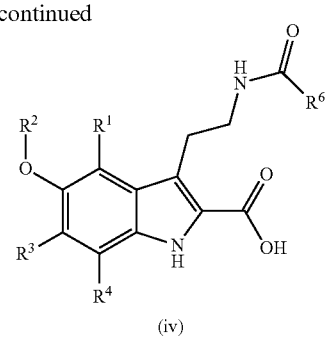

The present production process is a method for preparing the compound of the formula (iv), which is the starting compound of Production Process 1, in which Y is $CR^1$, X is a bond, and $R^7$ and $R^8$ are H in the compound (a).

(Step 1)

The present step is a preparation step in which a compound (i) is subjected to a reduction reaction to obtain a compound (ii).

In this reaction, the compound (i) is treated with a reducing agent in an equivalent amount or in an excess amount, in a solvent which is inert to the reaction, under cooling to heating, and preferably from −20° C. to 80° C., usually for 0.1 hours to 3 days. Examples of the solvent used herein are not particularly limited, but include ethers such as diethyl ether, tetrahydrofuran, dioxane, dimethoxyethane and the like, alcohols such as methanol, ethanol, 2-propanol and the like, aromatic hydrocarbons such as benzene, toluene, xylene and the like, N,N-dimethyl formamide, dimethyl sulfoxide, ethyl acetate, and a mixture thereof. As the reducing agent, hydride reducing agents such as sodium borohydride and the like, metal reducing agents such as sodium, zinc, iron and the like, reducing agents, and reducing agents described in the following documents are suitably used.

[References]

"Reductions in Organic Chemistry, $2^{nd}$ ed. (ACS Monograph: 188)" written by M. Hudlicky, ACS, 1996

"Comprehensive Organic Transformations" written by R. C. Larock, $2^{nd}$ edition, VCH Publishers, Inc., 1999

"Oxidation and Reduction in Organic Synthesis (Oxford Chemistry Primers 6)" written by T. J. Donohoe, Oxford Science Publications, 2000

"Courses in Experimental Chemistry" ($5^{th}$ edition) edited by The Chemical Society of Japan, Vol. 14 (2005) (Maruzen)

(Step 2)

The present step is a step in which a compound (ii) is subjected to a reduction reaction of a nitro group and further subjected to an amidation reaction to obtain a compound (iii).

In this reduction reaction, the compound (ii) is stirred in a solvent which is inert to the reaction, usually for 1 hour to 5 days, in the presence of a metal catalyst, under a hydrogen atmosphere. This reaction is carried out usually under cooling to heating, and preferably at room temperature. Examples of the solvent used herein are not particularly limited, but include alcohols such as methanol, ethanol, 2-propanol and the like, ethers such as diethyl ether, tetrahydrofuran, dioxane, dimethoxyethane and the like, water, ethyl acetate, N,N-dimethyl formamide, dimethyl sulfoxide, and a mixture thereof. As the metal catalyst, palladium catalysts such as palladium carbon, palladium black, palladium hydroxide and the like, platinum catalysts such as a platinum plate, platinum oxide and the like, nickel catalysts such as reduced nickel, Raney nickel and the like, rhodium catalysts such as tristriphenylphosphine chlororhodium and the like, and iron catalysts such as reduced iron and the like, and so forth are suitably used. This reaction can also be carried out using formic acid or ammonium formate in an equivalent amount or in an excess amount, relative to the compound (ii), as a hydrogen source instead of a hydrogen gas.

The reaction condition for the subsequent amidation reaction is the same as that for the Production Process 1 above.

In addition, the compound (iii) can be obtained by adding an amidation agent to the reaction system of the reduction reaction of the compound (ii) while not isolating an intermediate.

[References]

"Reductions in Organic Chemistry, $2^{nd}$ ed. (ACS Monograph: 188)" written by M. Hudlicky, ACS, 1996

"Courses in Experimental Chemistry" ($5^{th}$ edition) edited by The Chemical Society of Japan, Vol. 19 (2005) (Maruzen)

(Step 3)

The present step is a preparation step in which the compound (iii) is subjected to a hydrolysis reaction to obtain a compound (iv). Here, the hydrolysis reaction can be carried out with reference to "Protective Groups in Organic Synthesis" written by Greene and Wuts, $4^{th}$ edition, John Wiley & Sons Inc., 2006, as described above.

(Starting Material Synthesis 2)

[Chem. 15]

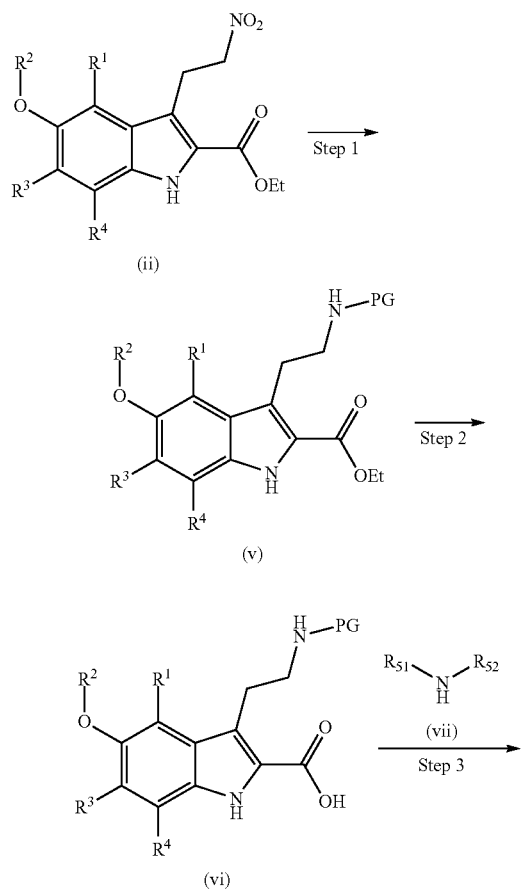

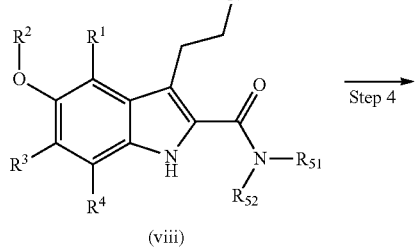

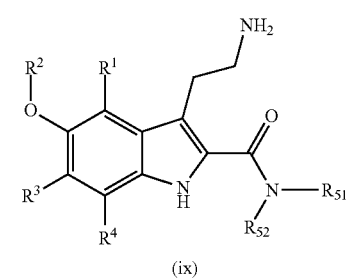

(wherein PG represents a protective group).

The present production process is a method for preparing a compound (ix), which is the starting compound of Production Process 2, in which Y is $CR^1$, and $R^7$ and $R^8$ are H in compound (c). The protection group PG includes t-butoxycarbonyl or the like.

(Step 1)

The present step is a preparation step in which a nitro group of the compound (ii) is subjected to a reduction reaction, and the resulting amine is protected with a protective group to obtain a compound (v). The reduction reaction of the nitro group is the same as the step 2 of Starting Material Synthesis 1. Further, the protection of the amine can be carried out with reference to "Protective Groups in Organic Synthesis" written by Greene and Wuts, $4^{th}$ edition, John Wiley & Sons Inc., 2006, as described above.

(Step 2)

The present step is a preparation step in which the compound (v) is subjected to a hydrolysis reaction to obtain a compound (vi). Here, the hydrolysis reaction can be carried out with reference to "Protective Groups in Organic Synthesis" written by Greene and Wuts, $4^{th}$ edition, John Wiley & Sons Inc., 2006, as described above.

(Step 3)

The present step is a preparation step in which the compound (vi) and the compound (vii) are subjected to an amidation reaction to obtain a compound (viii). The reaction condition is the same as that for Production Process 1.

(Step 4)

The present step is a step for preparing a compound (ix) in which the protective group of the compound (viii) is subjected to a deprotection reaction. The deprotection reaction can be carried out with reference to "Protective Groups in Organic Synthesis" written by Greene and Wuts, $4^{th}$ edition, John Wiley & Sons Inc., 2006, as described above.

25

(Starting Material Synthesis 3)

[Chem. 16]

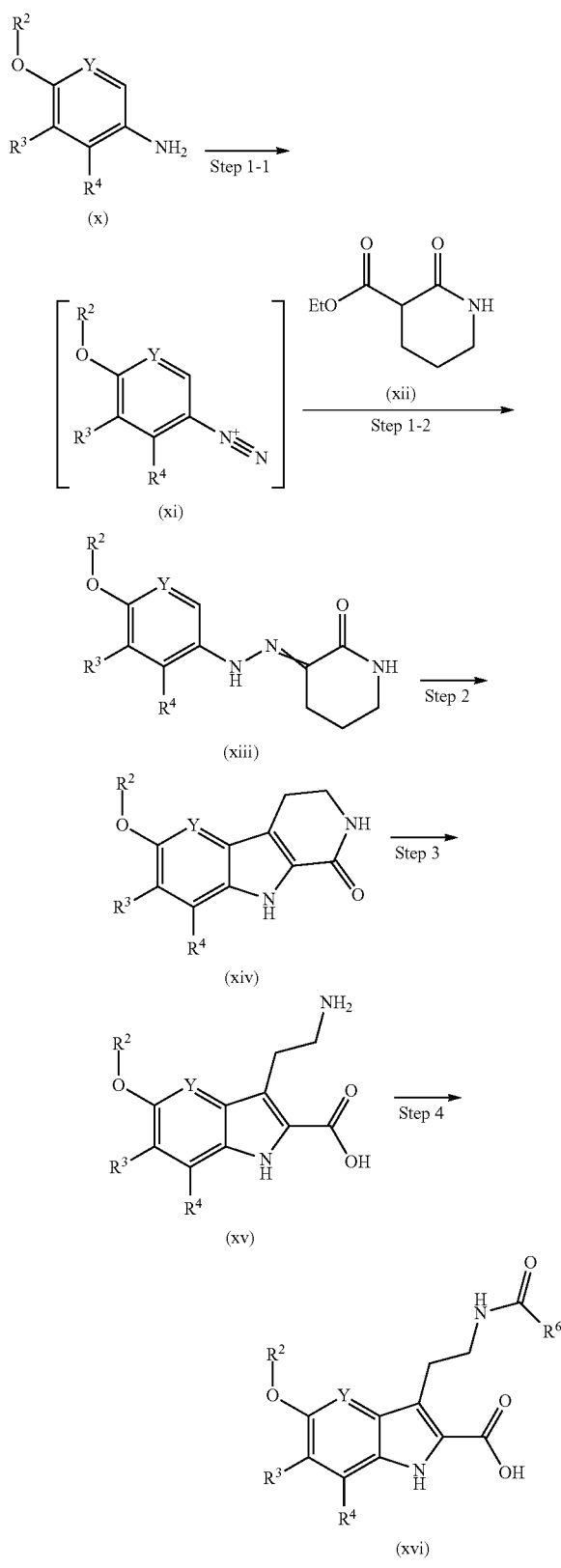

26

(wherein a compound of the formula (xiii) in which the double bonds are crossed represents a mixture of E and Z isomers, or either of the E isomer or the Z isomer).

The present production process is a method for preparing a compound (xvi), which is the starting compound of Production Process 1, in which X is a bond, and $R^7$ and $R^8$ are H in the compound (a).

(Step 1)

The present step is a preparation step of obtaining a compound (xiii) from a compound (x) and a compound (xii).

The present step is carried out using a nitrite under cooling, in a solvent which is inert to the reaction, in the presence of an acid, and the compound (x) is converted to the compound (xi) which is an intermediate. Then, the compound (xi) and the compound (xii) thus obtained can be reacted under cooling to heating, in the presence of an acid or a base, thereby obtaining the compound (xiii).

[References]

"Courses in Experimental Chemistry" (5th edition) edited by The Chemical Society of Japan, Vol. 14 (2005) (Maruzen)

(Step 2)

The present step is a step of obtaining a compound (xiv) from the compound (xiii). In the present step, the compound (xiii) is heated in a solvent which is inert to the reaction in the presence of an acid, and thus converted to the compound (xiv).

[References]

"Courses in Experimental Chemistry" (5th edition) edited by The Chemical Society of Japan, Vol. 14 (2005) (Maruzen)

(Step 3)

The present step is a preparation step in which a compound (xiv) is subjected to a hydrolysis reaction to obtain a compound (xv). The present step can be carried out with reference to "Protective Groups in Organic Synthesis" written by Greene and Wuts, 4th edition, John Wiley & Sons Inc., 2006, as described above.

(Step 4)

The present step is a preparation step in which the compound (xv) is subjected to an amidation reaction to obtain a compound (xvi). The present step can be carried out by reacting carboxylic anhydride with respect to the reaction compound (xv) in a solvent which is inert to the reaction in the presence of a base.

The pharmacological activity of the compound of the formula (I) was confirmed by the tests shown below.

Test Example 1 Test for Evaluating Activation of Human MT1 and Human MT2 Receptor by Test Compound Using Human MT1 and Human MT2 Receptor-Expressing Cells Experimental Method (1) Isolation of Human MT1 and MT2 Receptor and Construction of Expression Vector A human MT1 receptor gene (GenBank Accession No.: NM_005958.3) and a human MT2 receptor gene (GenBank Accession No.: NM_005959.3) were each introduced into an expression vector pCDNA3.1/Zeo (Invitrogen, Inc.).

(2) Construction of Cells Stably Expressing Human MT1 and Human MT2 Receptor

An expression vector of a human MT1 and human MT2 receptor was introduced into an HEK293 cell (ATCC No.: CRL-1573) together with a $G_{q/i}$ chimeric G-protein expression vector, respectively. The introduction was carried out according to the attached instructions, using a Lipofectoamine (registered trademark) 2000 Reagent (Invitrogen, Inc.). Zeocin and hygromycin were used as a resistant drug, and the cell was incubated for 15 days at 0.02 mg/mL and 0.05 mg/mL, respectively, thereby acquiring drug-resistant clones.

(3) Measurement of Intracellular $Ca^{2+}$ Concentration by FLIPR (Registered Trademark)

The respective stably expressing cells were dispensed into 96-well poly-D-lysine-coated plates (Falcon Co.) to 40,000 cells/well the day before the experiment, and incubated overnight in a DMEM (Invitrogen, Inc.) medium including 10% FBS at 37° C. and 5% $CO_2$. The medium was replaced with a loading buffer (washing solution (Hank's balanced salt solution (HBSS), 20 mM HEPES-NaOH, 2.5 mM probenecid) including Fluo-4AM (Dojindo Co.) at 4 μM), and incubated for 1 hour at 37° C. and 5% $CO_2$. Thereafter, the cells were washed with a plate washer (ELx405, BIO-TEK Instrument, Inc.) set with the washing solution, and set in an intracellular $Ca^{2+}$ concentration measuring systems (FLIPR (registered trademark), Molecular Device Co.). The test compound was dissolved in the washing solution in advance, diluted to a final concentration of −12 to −5 log M, set in a FLIPR (registered trademark) device together with the cells, and added to the cells in the device. At this time, a change in the intracellular $Ca^{2+}$ concentrations was measured.

For the agonistic activity, when a maximum reaction by ramelteon was taken as 100% and the reaction with only a solvent was taken as 0%, the activation action (Emax (%)) of the test compound with respect to the maximum reaction of ramelteon was determined and an efficacy ($EC_{50}$ (nM)) was calculated by a logistic regression method.

The $EC_{50}$ values and the Emax values of melatonin (purchased from Sigma) and ramelteon (purified from 8-mg tablets of Rozerem purchased from Takeda Pharmaceutical Co., Ltd.), and some Example compounds of the present invention are shown in Table 1. Ex represents Example No. of the test compound.

TABLE 1

| Test compound | MT1 | | MT2 | |
|---|---|---|---|---|
| | $EC_{50}$ (nM) | Emax (%) | $EC_{50}$ (nM) | Emax (%) |
| Melatonin | 1.1 | 94 | 4.3 | 91 |
| Ramelteon | 0.28 | 100 | 1.1 | 100 |
| Ex 1 | 12 | 104 | 26 | 108 |
| Ex 2 | 11 | 102 | 28 | 109 |
| Ex 8 | 12 | 124 | 19 | 119 |
| Ex 12 | 86 | 68 | 12 | 70 |
| Ex 15 | 5.4 | 104 | 17 | 103 |
| Ex 17 | 20 | 86 | 58 | 94 |
| Ex 32 | 7.7 | 106 | 31 | 111 |
| Ex 34 | 32 | 75 | 4.4 | 92 |
| Ex 35 | 3.2 | 110 | 11 | 102 |
| Ex 36 | 10 | 121 | 18 | 104 |
| Ex 48 | 12 | 122 | 43 | 109 |
| Ex 53 | 19 | 103 | 9.2 | 105 |

From the results above, it was confirmed that the Example compounds of the present invention have a human MT1 and/or human MT2 receptor agonistic activity.

Test Example 2 Isolated Urethra Contractile Action (1) Evaluation Test on Urethra Contractile Action of Test Compound Using Isolated Urethra Experimental Method The urethra was isolated from an SD female rat having a body weight of 100 to 500 g. The isolated urethra was incised longitudinally to give a rectangular strip specimen having a width of about 3 mm, which was suspended in the circular muscle direction in 10 mL of a tissue bath filled with a Krebs-Henseleit solution (pH 7.4). The Krebs-Henseleit solution was bubbled with 95% $O_2$ and 5% $CO_2$, and kept at 37° C. The resting tension was set to 0.5 g to record the isometric contraction. After the resting tension was stabilized, contraction was elicited by the addition of 10 μM phenylephrine. After washing and stabilizing, the test compound was added cumulatively to a final concentration of −12 to −5 log M to measure a contractile response. By taking the contractile response by 10 μM phenylephrine as 100%, the ratio of the contractile response in the concentration of the test compound at 1 μM was calculated.

The ratios of the contractile reaction in ramelteon and some Example compounds of the present invention are shown in Table 2. Ex represents Example No. of the test compound.

TABLE 2

| Test compound | Isolated urethra contraction (%) | Test compound | Isolated urethra contraction (%) |
|---|---|---|---|
| Ramelteon | 242 | Ex 17 | 132 |
| Ex 1 | 128 | Ex 32 | 143 |
| Ex 2 | 167 | Ex 35 | 171 |
| Ex 15 | 261 | Ex 36 | 107 |

Ramelteon and the Example compounds of the present invention exhibited a good urethra contractile action in the test using the isolated urethra.

(2) Test for Confirming that Urethra Contractile Action is Action Through MT1 and/or MT2 Receptor Experiment Method The urethra was isolated from an SD female rat having a body weight of 100 to 500 g. The isolated urethra was incised longitudinally to give a rectangular strip specimen having a width of about 3 mm, which was suspended in the muscle parallel to the circular to 10 mL of a tissue bath filled with a Krebs-Henseleit solution (pH 7.4). The Krebs-Henseleit solution was bubbled with 95% $O_2$ and 5% $CO_2$, and kept at 37° C. The resting tension was set to 0.5 g to record the isometric contraction. After the resting tension was stabilized, contraction was elicited by the addition of 10 μM phenylephrine. After washing and stabilizing, the test compound (ramelteon) at 1 μM was added to measure a contractile response. After washing and stabilizing, a solvent or Luzindole (purchased from Wako Pure Chemical Industries, Ltd.) (0.1 μM, 1 μM, or 10 μM) was added to the same specimen, and after 20 minutes, ramelteon at 1 μM was added again thereto to measure a contractile reaction. When the first contraction by ramelteon at 1 μM was taken as 100%, the second contractile rate by ramelteon was measured.

The second contractile rates by ramelteon when a solvent and Luzindole (0.1 μM, 1 μM, or 10 μM) were added are shown in Table 3.

TABLE 3

| Luzindole concentration (μM) | Second contractile rate by ramelteon (%) |
|---|---|
| 0 (solvent) | 98 ± 10 |
| 0.1 | 88 ± 11 |
| 1 | 75 ± 5 |
| 10 | 61 ± 9 |

The isolated urethra contractile action by ramelteon which is an MT1 and/or MT2 receptor agonist is inhibited in a concentration-dependent manner by the treatment with Luzindole which is a melatonin receptor antagonist. This result supports that the urethra contractile action by ramelteon is based on the melatonin receptor-activating action.

From the test results above, it was confirmed that the isolated urethra contractile action is an action through the MT1 and/or MT2 receptor and ramelteon and the Example compounds of the present invention, each having an MT1 and/or MT2 receptor agonistic action, has a urethra contractile action.

Test Example 3 Test to Evaluate Effect of Test Compound on Urethral Pressure

It has been reported that an increase in the urethra pressure is useful for the treatment of urinary incontinence, particularly stress urinary incontinence (for example, Drugs, 64, 14, 1503-1516 (2004)). In order to confirm whether the compound of the present invention increases the urethra pressure and thus is useful for the treatment of urinary incontinence, particularly stress urinary incontinence, the following tests were carried out.

Experiment Method

SD female rats were anesthetized with urethane and subjected to laparotomy. Then, the bladder apex was incised and a catheter was inserted from the bladder apex. Further, the catheter tip was ligated and fixed to be located in the proximal urethra portion. The catheter was connected to a pressure transducer and an infusion pump. Further, a catheter for administrating the compound was fitted into the femoral vein. Physiological saline was continuously infused into the urethra and the perfusion pressure in the urethra was measured. After the urethral pressure was stabilized, the test compound that had been dissolved in physiological saline, or physiological saline including 5% dimethylacetamide and 0.5% Cremophor was administered intravenously at 0.1 mg/kg, and a change in urethral pressures was measured.

Further, the results of administering an active metabolite of midodrine (ST-1059: purchased from CHEMIZON) (J. Urology, 118, 980-982 (1977)) which is an α1 adrenoceptor agonist and has an effect on stress urinary incontinence in rat doses (0.01 mg/kg) presumed to correspond to the clinical doses are referenced and shown in the Tables below. The increment value in the urethra pressures of ramelteon and the Example compounds of the present invention at the time of administration are shown in Table 4. Ex represents Example No. of the test compound.

TABLE 4

| Test compound | Increment value in the urethra pressures (mmHg) | Test compound | Increment value in the urethra pressures (mmHg) |
|---|---|---|---|
| ST-1059 | 4.9 ± 1.1 | Ex 17 | 9.0 ± 1.0 |
| Ramelteon | 11.1 ± 1.7 | Ex 32 | 10.8 ± 2.9 |
| Ex 1 | 5.1 ± 0.6 | Ex 35 | 8.2 ± 1.6 |
| Ex 2 | 10.6 ± 3.5 | Ex 36 | 7.3 ± 0.2 |
| Ex 8 | 6.0 ± 0.4 | Ex 48 | 7.3 ± 0.7 |
| Ex 15 | 8.6 ± 0.9 | Ex 53 | 10.5 ± 0.6 |

Ramelteon and the Example compounds of the present invention administration groups exhibited an increment value in the urethra pressures which is equal to or more than that of ST-1059. From this, it was suggested that ramelteon and the Example compounds of the present invention have a clinically significant action of increasing the urethra pressure.

Test Example 4 Test for Evaluating CNS Penetration (1) Measurement of Unbound Fraction (fp) in Rat Plasma A test compound (100 μg/mL, 50% acetonitrile solution) at 1% (v/v) with respect to the amount of the plasma was added to rat plasma, and dispensed to a sample for a supernatant and a sample for the plasma. The sample for a supernatant was ultracentrifuged at 436,000×g and 37° C. for 140 minutes, and the sample for the plasma was incubated at 37° C. for 140 minutes.

After 140 minutes, the sample for a supernatant after the ultracentrifugation and the sample for the plasma were taken, and mixed with the blank plasma or the blank supernatant, respectively. Acetonitrile including an internal standard material was added to each of the samples, and after the centrifugation at 2150×g and 4° C. for 10 minutes the supernatant was injected into LC-MS/MS.

The unbound fraction in the plasma was calculated by the following equation.

[Chem. 17]

$$fp = \frac{1/D}{1/(fu, app) - 1 + 1/D}$$

(wherein fp: an unbound fraction in the plasma and D: a dilution rate of the plasma.

fu,app=peak area ratio of supernatant sample/peak area ratio of the plasma sample, and peak area ratio=peak area of test compound/peak area of internal standard material).

(2) The CSF to Plasma Unbound Concentration Ratio in Rat

At 15 minutes after intravenously administration of the test compound to the rats, the plasma and CSF were collected. A 50% acetonitrile solution and an acetonitrile including internal standard material was added to the collected plasma or CSF. After centrifugation at 4° C. and 2150×g for 10 minutes, the supernatant was injected into LC-MS/MS, and the total concentration of the test compound in the plasma ($C_{plasma,t}$) and the concentration of the test compound in CSF ($C_{CSF}$) were obtained. The unbound concentration in the plasma ($C_{plasma,u}$) of the test compound and the CSF-to plasma unbound concentration ratio ($K_{p,uu,CSF}$) of the test compound was calculated by the following equation.

[Chem. 18]

$$C_{plasma,u} = fp \times C_{plasma,t}$$

$$K_{p,uu,CSF} = \frac{C_{CSF}}{C_{plasma,u}}$$

The $K_{p,uu,CSF,iv15min}$ values of ramelteon and some Example compounds of the present invention are shown in Table 5. Ex represents Example No. of the test compound.

TABLE 5

| Test compound | $K_{p,uu,CSF,iv15min}$ | Test compound | $K_{p,uu,CSF,iv15min}$ |
|---|---|---|---|
| ramelteon | 1.66* | Ex 8 | 0.03 |
| Ex 1 | 0.18 | Ex 15 | 0.07 |
| Ex 2 | 0.11 | Ex 17 | 0.08 |

(*Further, ramelteon represents the values of $K_{p,uu,CSF}$ after 10 minutes after the intravenous administration).

From the results above, it was found that ramelteon had a value of $K_{p,uu,CSF}$ of more than 1, a higher concentration in CSF than that in the plasma, and a high CNS penetration, whereas the Example compounds of the present invention had a lower CNS penetration than ramelteon with a value $K_{p,uu,CSF,iv15min}$ of 0.2 or less, as shown from the results above, and some Example compounds had a lower CNS penetration with the value of less than 0.1.

In addition, some test compounds were orally administered, and after 1 hour or 4 hours, CSF and the plasma were collected and the $K_{p,uu,CSF}$ values were calculated in the same manner, but the results were almost equal to the $K_{p,uu,CSF,iv15min}$ values.

(3) Brain-to-Plasma Concentration Ratio in Rat

At 15 minutes after intravenously administration of the test compound to the rats, the plasma and brain were collected. A 50% acetonitrile solution and an acetonitrile including internal standard material was added to the collected plasma. The collected brain was added a 2-fold volume of PBS and homogenized. A 50% acetonitrile solution and an acetonitrile including internal standard material was added thereto. The sample was centrifuged at 4° C. and 2150×g for 10 minutes, the supernatant was injected into LC-MS/MS, and the total concentration of the test compound in the brain ($C_{brain}$) and the total concentration of the test compound in the plasma ($C_{plasma,t}$) were obtained. The brain-to plasma concentrations ratio ($K_{p,brain}$) was calculated by the following equation.

[Chem. 19]

$$K_{p,brain} = \frac{C_{brain}}{C_{plasma,t}}$$

It was found that some Example compounds of the present invention had a $K_{p,brain}$ of less than 0.1 and a lower CNS penetration.

Test Example 5 Measurement Test of Electroencephalogram in Rat (1) Handling

In order to accustom the animals to operations during the experiment, handling was carried out for about 1 minute for one example once a day from the next day of the animal acquisition to the day before the administration.

(2) Method for Preparing Electroencephalogram Electrode-Implanted Specimen

After the completion of a quarantine period, the animals showing no abnormal health condition were subjected to an electroencephalogram electrode chronic implantation surgery with reference to brain atlas of Pellegrino et al. Under anesthesia with pentobarbital sodium (45 mg/kg, i.p.), the rat was calibrated in a brain stereotaxic apparatus. In the frontal cortex, a monopolar silver ball electrode having a diameter of the tip of about 1 mm was placed on a hard film of the brain. Into the hippocampus, a laminated bipolar electrodes made of stainless steel was stuck. The reference electrode was screwed around the olfactory brain. Further, as for the electromyogram measurement, the lead wire was implanted in the both electrodes about 1 cm between the electrodes in the neck portion. The other end was exposed to the head portion subcutaneously. The electrodes and the lead wires were subjected to soldering with connector sockets and fixed to the skull with a dental resin or the like.

(3) Sorting and Grouping of Animals

It was confirmed that twenty five rat examples which had been subjected to an electroencephalogram electrode chronic implantation surgery were recovered from the invasion of the surgery, and stable electroencephalogram were obtained therefrom. The weights of the animals were measured after 6 days from the surgery using an electronic scale balance the day before the first administration, and twenty rats were chosen in the descending order and distributed to perform administration. The administration order for the test materials was determined by a stratified random allocation method using a random number function of a spreadsheet software Excel (Microsoft Corporation).

(4) Measurement Method

The rats were accommodated in a measurement cage under rat feeding and water supply on the morning of the day of administration, and accustomed to the measurement environment. After measuring the weight using an electronic scale balance, a lead wire and a connector socket were connected 30 minutes or more before the start of the electroencephalogram measurement, and the rat was accustomed in the measurement state under no anesthesia and no custody. The test compounds (solvent, 0.1 mg/kg, 1 mg/kg, and 10 mg/kg) were intraperitoneally administered to the rats and the electroencephalogram was measured continuously until 6 hours after the administration.

The frequency of brain wave were acquired by applying electrical signals of electroencephalogram and of electromyogram an electroencephalogram system and using an electroencephalogram frequency analysis program of a personal computer from the electroencephalograph system. In addition, the image signals of the electroencephalogram waveform were applied to an EEG video system and recorded on a DVD recorder. The behavior observation was carried out through a video camera at the same time as the electroencephalogram measurement and the images were also recorded with the DVD recorder.

(5) Analysis Method (i) Spontaneous Electroencephalogram

The presence or absence of abnormality in the electroencephalogram waveform in up to 6 hours from immediately after the administration, to each animal, respectively, was observed.

(ii) Sleep-Awake Cycle

The analysis of a sleep-awake cycle was visually carried out using a sleep stage display-supporting program based on the electroencephalogram waveforms acquired with an electroencephalogram frequency analysis program. Using the index of electroencephalogram, electromyogram, and behavior, the sleep steps were classified into an awake phase, a rest phase, a slow wave light sleep (S.W.L.S.) phase, a slow wave deep sleep (S.W.D.S.) phase, and a fast wave sleep (F.W.S., REM sleep) phase. Further, the rest phase, the slow wave light sleep phase, and the slow wave deep sleep phase were summed to determine a slow wave sleep (S.W.S., Non-REM sleep) phase. The respective sleep steps (the awake phase, the rest phase, the slow wave light sleep phase, the slow wave deep sleep phase, and the fast wave sleep phase), classified in a 20-second unit for up to six hours after the administration from the completion of the administration, were displayed as a histogram. In addition, for the respective sleep steps, the occupancy up to six hours after the administration in a one-hour unit, a three-hour unit, and the total time (0 to 6 hours) were determined. As the assessment criteria in the respective sleep steps, the criteria described in Japanese Pharmacological Journal 84, 25-89 (1984) were used.

(6) Results

As a result of the electroencephalogram analysis test carried out using ramelteon, it was confirmed that there is a tendency that the occupancy of the sleep step of electroencephalogram from a dose of 0.1 mg/kg increases, the occupancy of the respective sleep step at 1 mg/kg significantly increases, and there is a sleep action. On the other hand, as a result of the test above carried out using the compound of Example 2 ($K_{p,uu,CSF,iv15min}$=0.11) of the present invention, it was confirmed that no change in the occupancy in the respective sleep steps of electroencephalogram could not be seen at any of the doses, and there was no sleep action. Further, as a result of the test above carried out using the compound of Example 17 ($K_{p,uu,CSF,iv15min}$=0.08), it was confirmed that no change in the occupancy in the respective sleep steps of electroencephalogram could not be seen with any of the doses, and there was no sleep action. This indicates that the concentration of the compound of the present invention in the brain does not reach the concentration expressing a sleep action even with a dose of 10 mg/kg. On the other hand, as shown in Test Example 3, it was confirmed that the compounds of Examples 2 and 17 of the present invention exhibit a good urethra pressure increasing action with a dose of 0.1 mg/kg, and thus, the compounds of the present invention having $K_{p,uu,CSF,iv15min}$ values of 0.11 and 0.08 shows a urethra pressure increasing action with a dose which does not exhibit a sleep action. These results demonstrates that the $K_{p,uu,CSF,iv15min}$ values are indicative of CNS penetration, the compounds of the present invention having a $K_{p,uu,CSF,iv15min}$ value of 0.11 or less does not exhibit an action on central nervous system disease in the dose having an action on urinary incontinence, and further, the compounds of Examples 2 and 17 does not exhibit a sleep action when administered in an effective dose in the application of treating urinary incontinence.

Test Example 6 Drug Pharmacokinetic Test, Safety Pharmacology Test, and Toxicity Test Using some Example compounds of the present invention, a drug Pharmacokinetic test, a safety pharmacology test, and a toxicity test were carried out.

(i) For the drug pharmacokinetic test, for example, evaluation of a cytochrome P450 (hereinafter referred to as CYP) inhibitory action was carried out. For the evaluation of the CYP inhibitory action, the method described in Analytical Biochemistry, 248, 188-190, (1997) or a method obtained by modification of the method described in the Document above was used.

(ii) For the safety pharmacology test, for example, evaluation of a Human Ether-a-go-go Related Gene (hereinafter referred to as hERG) channel inhibitory action was carried out. For the evaluation of the hERG channel inhibitory action, a method obtained by modification of the method described in Combinatorial Chemistry & High Throughput Screening, 12, 1, 78-95 (2009) was used.

(iii) For the toxicity test, for example, an in vitro phototoxicity test was carried out. The evaluation of the in vitro phototoxicity test was carried out in accordance with Guidance for industry photosafety testing, Center for Drug Evaluation and Research Food and Drug Administration, 2003, which is a guideline of FDA (U.S. Food and Drug Administration), and Note for guidance on photosafety testing (CPMP/SWP/398/01, 2002) which is a guideline of EMA (European Medicines Agency), and the method described in OECD guideline for testing of chemicals 432: In vitro 3T3 NRU phototoxicity test, 2004, which is a test method described in the report of OECD.

As a result of the drug Pharmacokinetic test, the safety pharmacology test, and the toxicity test, it was confirmed that the CYP1A2, 2C9, 2C19, 2D6, and 3A4 inhibitory action and the hERG channel inhibitory action of some Example compounds of the present invention are sufficiently weak.

In addition, in the phototoxicity test above, it was confirmed that the compounds of Examples 1, 2, 8, 15, and 17 have no phototoxicity action. Therefore, it was confirmed that the Example compounds of the present invention include clinically useful compounds.

By the tests above using some compounds of the formula (I), it was confirmed that the compound of the formula (I) has a urethra contractile action and a urethra pressure increasing action based on an MT1 and/or MT2 receptor agonistic action, and a low CNS penetration, and thus, the side effects risk of central nervous system is low. Therefore, the compound of the formula (I) can be used for the treatment of urological diseases; in one embodiment, lower urinary tract symptoms; in another embodiment, urine storage symptom; in a still another embodiment, urinary incontinence; and in a still further another embodiment, stress urinary incontinence, or the like.

A pharmaceutical composition comprising one or two or more kinds of the compound of the formula (I) or a salt thereof as an active ingredient, can be prepared using excipients that are usually used in the art, that is, excipients for pharmaceutical preparation, carriers for pharmaceutical preparation, and the like, according to the methods usually used.

Administration can be accomplished either by oral administration via tablets, pills, capsules, granules, powders, solutions, and the like, or parenteral administration via injections, such as intraarticular, intravenous, or intramuscular injections, and the like, suppositories, eye drops, eye ointments, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one or two or more kinds of the active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. In addition to the inert diluent, the liquid composition may also include auxiliary agents such as a solubilization assisting agent, a moistening agent, and a suspending agent, sweeteners, flavors, aromatics, and antiseptics.

The injections for parenteral administration include sterile aqueous or non-aqueous solution preparations, suspensions, or emulsions. The aqueous solvent includes, for example, distilled water for injection and physiological saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents include generally used ointment bases, lotion bases, aqueous or non-aqueous liquid preparations, suspensions, emulsions, and the like.

The transmucosal agents such as an inhaler, a transnasal agent, and the like, those in the form of a solid, liquid, or semi-solid state are used, can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device such as a measured administration inhalation device, and the like, or sprayer. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

Usually, in the case of oral administration, the daily dose is from about 0.001 to 100 mg/kg, preferably from 0.1 to 30 mg/kg, and more preferably from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the present invention comprises 0.01 to 100% by weight of, as an embodiment, 0.01 to 50% by weight of, one or more of the compound of the formula (I) or a salt thereof which is the active ingredient.

The compound of the formula (I) may be used in combination with various agents for preventing or treating diseases on which the compound of the formula (I) is considered to show the effect. Such the combined preparations may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples below. Further, the preparation methods for the starting compounds will be each described in Preparation Examples. In addition, the preparation methods for the compound of the formula (I) are not limited to the preparation methods of the specific Examples shown below, but the compound of the formula (I) can be prepared by a combination of these preparation methods or a method that is apparent to a person skilled in the art.

Furthermore, the following abbreviations may be used in some cases in Examples, Preparation Examples, and Tables below.

PEx: Preparation Example No., Ex: Example No., PSyn: Preparation Example No. prepared by the same method, Syn: Example No. prepared by the same method, Str: Structural chemical formula (Me represents methyl, Et represents ethyl, and Boc represents tert-butyloxycarbonyl), Data: Physico-chemical data, ESI+: m/z values in mass spectroscopy (Ionization ESI, representing [M+H]$^+$ unless otherwise specified), ESI−: m/z values (Ionization ESI, representing [M−H]$^-$ unless otherwise specified), APCI/ESI+: APCI/ESI-MS[M+H]$^+$ (atmospheric pressure chemical ionization APCI, and APCI/ESI means simultaneous measurement of APCI and ESI and represents [M+H]$^+$ unless otherwise specified), APCI/ESI−: APCI/ESI-MS[M−H]$^-$ (atmospheric pressure chemical ionization APCI, and APCI/ESI means simultaneous measurement of APCI and ESI and represents [M−H]$^-$ unless otherwise specified), FAB+: m/z values in mass spectroscopy (Ionization FAB, representing [M+H]$^+$ unless otherwise specified), EI: EI[M]+, 1H-NMR (DMSO-d$_6$): peak δ (ppm) in $^1$H NMR in DMSO-d$_6$, 1H-NMR (CDCl$_3$): peak δ (ppm) in $^1$H NMR in CDCl$_3$, s: singlet (spectrum), d: doublet (spectrum), t: triplet (spectrum), q: quartet (spectrum), br: broad line (spectrum) (e.g.: brs), m: multiplet (spectrum), and m. p.: a melting point measured by a Yanaco Micro Melting Point Apparatus MP500D. Further, in the case where both of compounds represented by two structural formulae are shown as a Preparation Example compound, an additional description 'and' in the structural formula denotes that the compounds represented by the structural formulae are obtained as a mixture, and an additional description 'or in the structural formula denotes that the compounds represented by the structural formulae are obtained as either one of the two compounds. In addition, HCl in the structural formula represents that the compound is monohydrochloride.

Further, in the present specification, a nomenclature software such as ACD/Name (registered trademark, Advanced Chemistry Development, Inc.) may be used for nomenclature of compounds in some cases.

In addition, for a convenience, a concentration of mol/L is represented by M. For example, a 1 M aqueous sodium hydroxide solution means a 1 mol/L aqueous sodium hydroxide solution.

Preparation Example 1

To a mixture of ethyl 5-methoxy-3-[(E)-2-nitrovinyl]-1H-indole-2-carboxylate (4.92 g) and ethanol (100 mL) was added sodium borohydride (1.92 g), followed by stirring at room temperature for 2 hours. To the mixture were added acetic acid and then water under ice-cooling, and the precipitated solid was collected by filtration and dried to obtain ethyl 5-methoxy-3-(2-nitroethyl)-1H-indole-2-carboxylate (4.01 g) as a yellow solid.

Preparation Example 2

A mixed solution of ethyl 5-methoxy-3-(2-nitroethyl)-1H-indole-2-carboxylate (500 mg), tetrahydrofuran (40.0 mL), and acetic anhydride (2.00 mL) was pumped through Raney nickel cartridge, using H-cube (registered trademark) (ThalesNano Inc.) apparatus (catalyst cartridge: CatCart (registered trademark) (ThalesNano Inc.) hydrogen pressure: 60 bar, reaction temperature: 60° C., flow rate: 1 mL/s, solution concentration: 0.05 M). The obtained mixture was concentrated under reduced pressure and the obtained residue was washed with a mixed solvent of hexane:ethyl acetate=2:1 to obtain ethyl 3-(2-acetamidoethyl)-5-methoxy-1H-indole-2-carboxylate (450 mg) as a white solid.

Preparation Example 3

To a mixture of ethyl 3-(2-acetamidoethyl)-5-methoxy-1H-indole-2-carboxylate (350 mg), tetrahydrofuran (5.00 mL), and ethanol (5.00 mL) was added a 1 M aqueous sodium hydroxide solution (2.00 mL), followed by stirring at room temperature for 1 hour. The solvent was evaporated under reduced pressure, and the obtained residue was dissolved in water and adjusted to be weakly acidic by the addition of 1 M hydrochloric acid. The precipitated solid was collected by filtration and then dried to obtain 3-(2-acetamidoethyl)-5-methoxy-1H-indole-2-carboxylic acid (300 mg) as a gray solid.

Preparation Example 4

To a mixture of ethyl 5-methoxy-3-(2-nitroethyl)-1H-indole-2-carboxylate (850 mg), di-tert-butyl dicarbonate (2.54 g), and tetrahydrofuran (60.0 mL) was added Raney nickel (85.0 mg), followed by stirring at 60° C. for 3 hours under a hydrogen atmosphere (3.5 kgf/cm$^2$). The reaction mixture was filtered through celite and the filtrate was concentrated under reduced pressure. The obtained residue was purified by silica gel column chromatography (hexane:ethyl acetate=100:0 to 2:1) to obtain ethyl 3-{2-[(tert-butoxycarbonyl)amino]ethyl}-5-methoxy-1H-indole-2-carboxylate (761 mg) as a white solid.

Preparation Example 5

To a mixture of 3-{2-[(tert-butoxycarbonyl)amino]ethyl}-5-methoxy-1H-indole-2-carboxylic acid (500 mg), diisopropylethylamine (1.28 mL), methylamine hydrochloride (303 mg), and N,N-dimethyl formamide (10.0 mL) was added 2-(7-aza-1H-benzotriazol-1-yl)-1,1,3,3-tetramethyluronium hexafluorophosphate (853 mg), followed by stirring at room temperature overnight. To the mixture was added ice water, followed by extraction with ethyl acetate, and the organic layer was washed with saturated brine, and dried over anhydrous sodium sulfate. The insoluble materials were separated by filtration, the filtrate was concentrated under reduced pressure, and the obtained residue was purified by silica gel column chromatography (chloroform:methanol=100:0 to 20:1) to obtain tert-butyl {2-[5-methoxy-2-(methylcarbamoyl)-1H-indol-3-yl]ethyl}carbamate (520 mg) as a white solid.

Preparation Example 6

To a mixture of tert-butyl {2-[5-methoxy-2-(methylcarbamoyl)-1H-indol-3-yl]ethyl}carbamate (520 mg) and dioxane (5.00 mL) was added hydrogen chloride (4 M dioxane solution, 5.00 mL), followed by stirring at room temperature for 3 hours. The reaction mixture was concentrated under reduced pressure to obtain 3-(2-aminoethyl)-5-methoxy-N-methyl-1H-indole-2-carboxamide hydrochloride (460 mg) as a yellow solid.

Preparation Example 7

To a mixture of 3-{2-[(difluoroacetyl)amino]ethyl}-5-methoxy-N-methyl-1H-indole-2-carboxamide (2.52 g) and dichloromethane (50.0 mL) was added boron tribromide (1.0 M dichloromethane solution, 23.3 mL) under ice-cooling, followed by slowly warming to room temperature, and then stirring at room temperature overnight. The reaction mixture was cooled to −15° C. and methanol (5.00 mL) was added thereto, followed by warming to room temperature. The reaction mixture was concentrated under reduced pressure and then the residue was purified by silica gel column chromatography (chloroform:methanol=100:0 to 5:1) to obtain 3-{2-[(difluoroacetyl)amino]ethyl}-5-hydroxy-N-methyl-1H-indole-2-carboxamide (2.37 g) as a yellow solid.

Preparation Example 8

To an aqueous solution (30.0 mL) of 3-fluoro-4-methoxyaniline (2.00 g) was added concentrated hydrochloric acid (3.20 mL). To the mixture was added an aqueous solution (30.0 mL) of sodium nitrite (1.12 g) slowly under ice-cooling, followed by stirring for 30 minutes. To the mixture was added a 10% aqueous sodium carbonate solution, followed by adjusting the pH to 4.5 (Solution A). Potassium hydroxide (954 mg) was added to and dissolved in water (30.0 mL), followed by adding ethyl 2-oxopiperidine-3-carboxylate (2.58 g) and stirring at room temperature overnight (Solution B). To the Solution B was added the Solution A under ice-cooling, followed by stirring for 4 hours under ice-cooling. The precipitated solid was collected by filtration and dried to obtain 3-[(3-fluoro-4-methoxyphenyl)hydrazinylidene)]piperidin-2-one (a mixture of E and Z isomers) (2.45 g) as a yellow solid.

Preparation Example 9

A mixture of 3-[(3-fluoro-4-methoxyphenyl)hydrazinylidene]piperidin-2-one (a mixture of E and Z isomers) (2.45 g) and formic acid (25.0 mL) was stirred at 100° C. for 1 hour. The reaction mixture was cooled to room temperature, and then water (40.0 mL) was added thereto, followed by extraction with ethyl acetate. The organic layer was washed with saturated brine and dried over anhydrous sodium sulfate. The insoluble materials were separated by filtration, the filtrate was concentrated under reduced pressure, and the residue was purified by silica gel column chromatography (chloroform:methanol=10:0 to 10:1) to obtain 7-fluoro-6-methoxy-2,3,4,9-tetrahydro-1H-pyrido[3,4-b]indol-1-one (780 mg) as a brown solid.

Preparation Example 10

To a mixture of 7-fluoro-6-methoxy-2,3,4,9-tetrahydro-1H-pyrido[3,4-b]indol-1-one (780 mg), ethanol (5.00 mL), and water (5.00 mL) was added potassium hydroxide (1.58 g), followed by stirring at 80° C. overnight. Potassium hydroxide (1.58 g) was added to the reaction mixture, followed by stirring at 100° C. for 6 hours. After cooling to room temperature, the solvent was evaporated under reduced pressure. The obtained residue was dissolved in water (10.0 mL), to the mixture was added acetic acid (3.00 mL), and the precipitated solid was collected by filtration and dried under reduced pressure to obtain 3-(2-aminoethyl)-6-fluoro-5-methoxy-1H-indole-2-carboxylic acid (607 mg) as a reddish brown solid.

Preparation Example 11

To a mixture of 3-(2-aminoethyl)-6-fluoro-5-methoxy-1H-indole-2-carboxylic acid (150 mg) and tetrahydrofuran (1.88 mL) were added diisopropylethylamine (0.204 mL) and difluoroacetic anhydride (0.073 mL), followed by stirring for 3 hours. To the mixture was further added difluoroacetic anhydride (0.073 mL), followed by stirring for 3 hours. To the mixture was added difluoroacetic anhydride (0.073 mL), followed by stirring at room temperature overnight. To the mixture was added a saturated aqueous sodium hydrogen carbonate solution, followed by stirring for 1 hour, and the solvent was evaporated under reduced pressure. To the obtained residue was added water, followed by adjusting it to be weakly acidic by the addition of 1 M hydrochloric acid. This mixture was extracted with ethyl acetate, and the organic layer was washed with saturated brine and then dried over anhydrous sodium sulfate. The insoluble materials were separated by filtration and the filtrate was concentrated under reduced pressure to obtain 3-{2-[(difluoroacetyl)amino]ethyl}-6-fluoro-5-methoxy-1H-indole-2-carboxylic acid (182 mg) as a brown solid.

Preparation Example 12

To a mixture of 7-chloro-6-methoxy-2,3,4,9-tetrahydro-1H-pyrido[3,4-b]indol-1-one (2.35 g), ethanol (15.0 mL), and water (15.0 mL) was added potassium hydroxide (8.94 g), followed by stirring at 80° C. overnight. After cooling to room temperature, the solvent was evaporated under reduced pressure, and water was added to the residue. Further, acetic acid (about 8.00 mL) and then di-tert-butyl dicarbonate (1.64 g) were added thereto, followed by stirring at room temperature for 1 hour. The reaction mixture was adjusted to be weakly acidic with 1 M hydrochloric acid, and then extracted with ethyl acetate. The organic layer was washed with saturated brine and dried over anhydrous sodium sulfate. The insoluble materials were separated by filtration, the filtrate was concentrated under reduced pressure, and the obtained residue was purified by silica gel column chromatography (chloroform:formic acid (10% methanol solution)=10:0 to 10:1) to obtain 3-{2-[(tert-butoxycarbonyl)amino]ethyl}-6-chloro-5-methoxy-1H-indole-2-carboxylic acid (1.70 g) as a pale yellow solid.

Preparation Example 13

A mixture of 1-(allyloxy)-2-chloro-4-nitrobenzene (55.2 g) and N,N-diethylaniline (50.0 mL) was stirred at 210° C. for 6 hours, and then followed by stirring at 175° C. overnight. At room temperature, the pH of the reaction mixture was adjusted to 1 by the addition of concentrated hydrochloric acid, followed by extraction with ether. The organic layer was washed with saturated brine and then dried over anhydrous sodium sulfate, the insoluble materials were separated by filtration, and the filtrate was concentrated under reduced pressure. The obtained residue was purified by silica gel column chromatography (hexane:ethyl acetate=100:0 to 88:12) to obtain 2-allyl-6-chloro-4-nitrophenol (30.1 g) as a yellow solid.

Preparation Example 14

To a mixture of 2-allyl-6-chloro-4-nitrophenol (30.0 g), acetone (270 mL), and water (30.0 mL) were added a 2.5 wt % osmium (VIII) oxide solution in tert-butanol (10.0 mL) and 4-methylmorpholin-4-oxide (18.1 g), followed by stirring at room temperature for 41 hours. The reaction mixture was concentrated under reduced pressure, acidified with 1 M hydrochloric acid, and extracted with ethyl acetate. The organic layer was washed with saturated brine and then dried over anhydrous sodium sulfate. The insoluble materials were separated by filtration, the filtrate was concentrated under reduced pressure, and the obtained solid was washed with a mixed solvent of chloroform and hexane to obtain 3-(3-chloro-2-hydroxy-5-nitrophenyl)propane-1,2-diol (20.8 g).

Preparation Example 15

To a mixture of 3-(3-chloro-2-hydroxy-5-nitrophenyl)propane-1,2-diol (18.7 g), tetrahydrofuran (300 mL), and water (150 mL) was added sodium periodate (19.3 g) under ice-cooling, followed by stirring for 3 hours under ice-cooling. To this mixture was carefully added sodium borohydride (5.70 g) under ice cooling while maintaining the internal temperature at 10° C. or lower, followed by stirring for 1 hour. To this mixture was added sodium borohydride (2.85 g), followed by stirring for 30 minutes, and then acidified under ice cooling by the slow addition of 1 M hydrochloric acid, followed by extraction with ethyl acetate. The organic layer was washed with saturated brine and dried over anhydrous sodium sulfate, then the insoluble materials were separated by filtration, and the filtrate was concentrated under reduced pressure. The obtained residue was purified by silica gel column chromatography (hexane:ethyl acetate=100:0 to 60:40) to obtain 2-chloro-6-(2-hydroxyethyl)-4-nitrophenol (11.5 g) as a yellow solid.

Preparation Example 16

A mixture of 2-chloro-6-(2-hydroxyethyl)-4-nitrophenol (11.3 g) and pyridine (41.8 mL) was cooled to −15° C. To this mixture was added dropwise methanesulfonyl chloride (4.04 mL), followed by stirring at −10° C. for 30 minutes. To this reaction mixture was added methanesulfonyl chloride (2.02 mL), followed by stirring at −10° C. for 20 minutes. To the mixture was added a saturated aqueous sodium hydrogen carbonate solution, followed by stirring for 2 hours, the pH was adjusted to 1 with 6 M hydrochloric acid, followed by extraction with ethyl acetate, and the organic layer was washed with saturated brine and then dried over anhydrous sodium sulfate. The insoluble materials were separated by filtration, the filtrate was concentrated under reduced pressure, and then the obtained residue was dissolved in ethyl acetate. To this mixture was added triethylamine (18.1 mL), followed by stirring at 78° C. overnight. After cooling to room temperature, the reaction mixture was concentrated under reduced pressure, and the obtained residue was purified by silica gel column chromatography (hexane:ethyl acetate=100:0 to 70:30) to obtain 7-chloro-5-nitro-2,3-dihydro-1-benzofuran (7.75 g) as a yellow solid.

Preparation Example 17

To a mixture of 7-chloro-5-nitro-2,3-dihydro-1-benzofuran (7.40 g) and ethanol (300 mL) were added reduced iron (12.4 g) and concentrated hydrochloric acid (20.0 mL) under ice-cooling, followed by warming to room temperature and stirring overnight. This mixture was neutralized with a saturated aqueous sodium hydrogen carbonate solution and sodium hydrogen carbonate under ice-cooling, filtered through celite, and then extracted with ethyl acetate. The organic layer was washed with saturated brine and then dried over anhydrous sodium sulfate, the insoluble materials were separated by filtration, and the filtrate was concentrated under reduced pressure. The obtained residue was purified by silica gel column chromatography (hexane:ethyl acetate=80:20 to 60:40) to obtain 7-chloro-2,3-dihydro-1-benzofuran-5-amine (5.49 g) as a pale yellow solid.

Preparation Example 18

To a mixture of a mixture (1.74 g) of 4-chloro-1,2,6,8,9,10-hexahydro-7H-furo[3,2-e]pyrido[3,4-b]indol-7-one and 10-chloro-2,3,5,7,8,9-hexahydro-6H-furo[2,3-f]pyrido[3,4-b]indol-6-one, and ethanol (20.0 mL) was added a 50% aqueous sodium hydroxide solution (20.0 mL), followed by warming to 80° C. and stirring overnight. This mixture was warmed to 100° C. and stirred for 2 days. The reaction mixture was ice-cooled, and then tetrahydrofuran (40.0 mL) and water (40.0 mL) were added thereto. A solution of di-tert-butyl dicarbonate (1.44 g) in tetrahydrofuran (40 mL) was further added thereto, followed by stirring at room temperature overnight. To the mixture was added di-tert-butyl dicarbonate (13.0 g), followed by stirring at room temperature overnight. The reaction mixture was neutralized (ca. pH 8) with acetic acid, and sodium hydrogen carbonate (2.78 g) was added thereto. Di-tert-butyl dicarbonate (2.16 g) was further added thereto, followed by stirring at room temperature for 2 days. The pH of the reaction mixture was adjusted to 3 with acetic acid and 6 M hydrochloric acid, followed by extraction with ethyl acetate. The organic layer was washed with saturated brine and dried over anhydrous sodium sulfate, and then the insoluble materials were separated by filtration. The filtrate was concentrated under reduced pressure and then the obtained residue was washed with a solution of hexane:ethyl acetate=5:1 to obtain a mixture (1.85 g) of 8-{2-[(tert-butoxycarbonyl)amino]ethyl}-4-chloro-1,6-dihydro-2H-furo[3,2-e]indole-7-carboxylic acid and 7-{2-[(tert-butoxycarbonyl)amino]ethyl}-8-chloro-3,5-dihydro-2H-furo[2,3-f]indole-6-carboxylic acid as a yellowish brown solid.

Preparation Example 19

To a mixture of a mixture (1.48 g) of 4-fluoro-1,2,6,8,9,10-hexahydro-7H-furo[3,2-e]pyrido[3,4-b]indol-7-one and 10-fluoro-2,3,5,7,8,9-hexahydro-6H-furo[2,3-f]pyrido[3,4-b]indol-6-one, and ethanol (20.0 mL) was added a mixture of potassium hydroxide (11.0 g) and water (10.0 mL), followed by warming to 100° C. and stirring for 2 days. The reaction mixture was ice-cooled and then neutralized with acetic acid (9.63 mL). Sodium hydrogen carbonate (5.05 g) and then di-tert-butyl dicarbonate (2.05 g) were added thereto. After stirring at room temperature for 2 days, the pH of the reaction mixture was adjusted to 3 with acetic acid and 6 M hydrochloric acid, followed by extraction with ethyl acetate. The organic layer was washed with saturated brine and then dried over anhydrous sodium sulfate, the insoluble materials were separated by filtration, and the filtrate was concentrated under reduced pressure to obtain a mixture (2.55 g) of 6-(tert-butoxycarbonyl)-8-{2-[(tert-butoxycarbonyl)amino]ethyl}-4-fluoro-1,6-dihydro-2H-furo[3,2-e]indole-7-carboxylic acid and 5-(tert-butoxycarbonyl)-7-{2-[(tert-butoxycarbonyl)amino]ethyl}-8-fluoro-3,5-dihydro-2H-furo[2,3-f]indole-6-carboxylic acid.

Preparation Example 20

To a mixture of tert-butyl {2-[5-bromo-7-(methylcarbamoyl)-1,6-dihydro-2H-furo[3,2-e]indol-8-yl]ethyl}carbamate (569 mg), triethylamine (0.724 mL), tetrahydrofuran (10.0 mL), and ethanol (30.0 mL) was added 10% palladium on carbon (50% water included, 284 mg) under an argon gas flow, followed by stirring at room temperature overnight under a hydrogen atmosphere (3.2 kgf/cm$^2$). The catalyst was separated by filtration and the filtrate was concentrated under reduced pressure to obtain tert-butyl {2-[7-(methylcarbamoyl)-1,6-dihydro-2H-furo[3,2-e]indol-8-yl]ethyl}carbamate (434 mg) as a pale yellow solid.

Preparation Example 21

To a mixture of 2,3-dihydro-1-benzofuran-5-carboxylic acid (5.08 g), triethylamine (5.18 mL) and tert-butanol (91.9 mL) was added diphenylphosphoryl azide (8.00 mL), followed by stirring at 90° C. for 5 hours. The reaction mixture was poured into a saturated aqueous sodium hydrogen carbonate solution, followed by extraction with ethyl acetate. The organic layer was washed with a saturated aqueous sodium hydrogen carbonate solution and saturated brine, and dried over anhydrous sodium sulfate. The insoluble materials were separated by filtration, the filtrate was concentrated under reduced pressure, and the obtained residue was purified by silica gel column chromatography (hexane:ethyl acetate=20:1 to 5:1) to obtain tert-butyl (2,3-dihydro-1-benzofuran-5-yl)carbamate (4.74 g).

Preparation Example 22

To a mixture of tert-butyl (2,3-dihydro-1-benzofuran-5-yl)carbamate (410 mg) and acetonitrile (9.00 mL) was added N-bromosuccinimide (341 mg), followed by stirring at 65° C. for 1 hour. After cooling to room temperature, the reaction mixture was poured into a saturated aqueous sodium hydrogen carbonate solution, followed by extraction with ethyl acetate. The organic layer was washed with saturated brine and dried over anhydrous sodium sulfate. The insoluble materials were separated by filtration, the filtrate was concentrated under reduced pressure, and then the obtained residue was purified by silica gel column chromatography (hexane:ethyl acetate=100:0 to 92:8) to obtain tert-butyl (6-bromo-2,3-dihydro-1-benzofuran-5-yl)carbamate (178 mg) as a colorless solid.

Preparation Example 23

To a mixture of tert-butyl (6-bromo-2,3-dihydro-1-benzofuran-5-yl)carbamate (2.75 g) and dioxane (15.0 mL) was added hydrogen chloride (4 M dioxane solution, 15.0 mL), followed by stirring at room temperature overnight. The solvent was evaporated under reduced pressure to obtain 6-bromo-2,3-dihydro-1-benzofuran-5-amine hydrochloride (2.23 g) as a pale yellow solid.

Preparation Example 24

A mixture of 3-[(6-bromo-2,3-dihydro-1-benzofuran-5-yl)hydrazinylidene]piperidin-2-one (a mixture of E and Z isomers)(137 mg) and acetic acid (3.00 mL) was stirred at 115° C. for 4 hours. After cooling to room temperature, the reaction mixture was concentrated under reduced pressure and the obtained residue was purified by silica gel chromatography (chloroform:methanol=100:0 to 96:4) to obtain 5-bromo-1,2,6,8,9,10-hexahydro-7H-furo[3,2-e]pyrido[3,4-b]indol-7-one (40.0 mg) as a red solid.

Preparation Example 25

To a mixture of 8-(2-aminoethyl)-5-bromo-1,6-dihydro-2H-furo[3,2-e]indole-7-carboxylic acid (523 mg), tetrahydrofuran (2.00 mL), and water (2.00 mL) were added sodium hydrogen carbonate (540 mg) and di-tert-butyl dicarbonate (456 mg), followed by stirring at room temperature overnight. The reaction mixture was concentrated under reduced pressure, then the residue was acidified with 1 M hydrochloric acid, and the precipitated solid was collected by filtration and dried under reduced pressure to obtain 5-bromo-8-{2-[(tert-butoxycarbonyl)amino]ethyl}-1,6-dihydro-2H-furo[3,2-e]indole-7-carboxylic acid (622 mg) as a beige solid.

Preparation Example 26

To a mixture of a mixture (1.85 g) of 8-{2-[(tert-butoxycarbonyl)amino]ethyl}-4-chloro-1,6-dihydro-2H-furo[3,2-e]indole-7-carboxylic acid and 7-{2-[(tert-butoxycarbonyl)amino]ethyl}-8-chloro-3,5-dihydro-2H-furo[2,3-f]indole-6-carboxylic acid, and diisopropylethylamine (4.16 mL), methylamine hydrochloride (988 mg), and N,N-dimethyl formamide (37.0 mL) was added 2-(7-aza-1H-benzotriazol-1-yl)-1,1,3,3-tetramethyluronium hexafluorophosphate (2.77 g), followed by stirring at room temperature overnight. To the mixture was added water under ice-cooling, and the precipitated solid was collected by filtration and dried under reduced pressure to obtain a yellowish brown solid. This was purified by silica gel column chromatography (toluene:chloroform: methanol=5:4:0 to toluene:chloroform:methanol=50:40:6) to obtain tert-butyl {2-[4-chloro-7-(methylcarbamoyl)-1,6-dihydro-2H-furo[3,2-e]indol-8-yl]ethyl}carbamate (213 mg) of a high-polarity fraction as a compound of Preparation Example 26. Further, the low-polarity fraction was concentrated under reduced pressure and the obtained residue was solidified with ethanol to obtain a yellow solid of tert-butyl {2-[8-chloro-6-(methylcarbamoyl)-3,5-dihydro-2H-furo[2,3-f]indol-7-yl]ethyl}carbamate (750 mg) as a compound of Preparation Example 66 as shown in the table below.

Preparation Example 27

To an aqueous solution (30.0 mL) of 3-bromo-4-methoxyaniline (2.60 g) was added concentrated hydrochloric acid (3.14 mL). To this mixture was slowly added an aqueous solution (30.0 mL) of sodium nitrite (1.02 g) under ice-cooling, followed by stirring for 30 minutes. The pH of this mixture was adjusted to 4.5 by the addition of a 10% aqueous sodium carbonate solution (Solution A). Potassium hydroxide (866 mg) was added to and dissolved in water (30.0 mL), and then ethyl 2-oxo piperidine-3-carboxylate (2.35 g) was added thereto, followed by stirring at room temperature overnight (Solution B). To the Solution B was added the Solution A under ice-cooling, and the pH was adjusted to 5 by the addition of acetic acid, followed by stirring for 4 hours under ice-cooling and then stirring at room temperature overnight. The precipitated solid was collected by filtration and dried under reduced pressure to obtain a yellow solid (3.04 g). A mixture of the obtained solid (3.04 g) and formic acid (25.0 mL) was stirred at 100° C. for 1 hour. The reaction mixture was cooled to room temperature and then concentrated under reduced pressure, and the obtained residue was purified by silica gel column chromatography (chloroform:methanol=10:0 to 10:1) to obtain 7-bromo-6-methoxy-2,3,4,9-tetrahydro-1H-pyrido[3,4-b]indol-1-one (1.92 g) as a brown solid.

Preparation Example 28

To a mixture of 8-fluoro-6-methoxy-2,3,4,9-tetrahydro-1H-pyrido[3,4-b]indol-1-one (1.35 g) and ethanol (5.00 mL) was added a 50% aqueous sodium hydroxide solution (5.00 mL), followed by stirring at 100° C. overnight. After cooling to room temperature, a solution of di-tert-butyl dicarbonate (2.00 g) in tetrahydrofuran (5.00 mL) was added thereto, followed by stirring at room temperature for 10 minutes. The reaction mixture was adjusted to be weakly acidic with 1 M hydrochloric acid, followed by extraction with ethyl acetate. The organic layer was washed with saturated brine and dried over anhydrous sodium sulfate. The insoluble materials were separated by filtration, the filtrate was concentrated under reduced pressure, and the obtained residue was purified by silica gel column chromatography (chloroform:formic acid (10% methanol solution)=10:0 to 10:1) to obtain a pale yellow solid (550 mg). To a mixture of the obtained solid (550 mg), diisopropylethylamine (1.41 mL), methylamine hydrochloride (333 mg), and N,N-dimethyl formamide (21.7 mL) was added 2-(7-aza-1H-benzotriazol-1-yl)-1,1,3,3-tetramethyluronium hexafluorophosphate (938 mg), followed by stirring at room temperature overnight. To the mixture was added ice water, followed by extraction with ethyl acetate, and the organic layer was washed with saturated brine and dried over anhydrous sodium sulfate. The insoluble materials were separated by filtration, the filtrate was concentrated under reduced pressure, and the obtained residue was purified by silica gel column chromatography (chloroform:methanol=10:0 to 10:1) to obtain tert-butyl {2-[7-fluoro-5-methoxy-2-(methylcarbamoyl)-1H-indol-3-yl]ethyl}carbamate (185 mg) as a white solid.

Preparation Example 29

To a mixture of 3-(2-aminoethyl)-4,6-difluoro-5-methoxy-1H-indole-2-carboxylic acid (2.45 g) and tetrahydrofuran (73.5 mL) were added a 1 M aqueous sodium hydroxide solution (18.1 mL) and water (15.0 mL). To this mixture was added di-tert-butyl dicarbonate (2.97 g), followed by stirring at room temperature for 2 hours. The reaction mixture was concentrated under reduced pressure and then to the obtained residue was added water, followed by neutralization with 1 M hydrochloric acid. The precipitated solid was collected by filtration and dried under reduced pressure to obtain 3-{2-[(tert-butoxycarbonyl)amino]ethyl}-4,6-difluoro-5-methoxy-1H-indole-2-carboxylic acid (3.35 g) as a white solid.

Preparation Example 30

To a mixture of 3-(1-aminopropan-2-yl)-5-methoxy-1H-indole-2-carboxylic acid (1.00 g), 1 M aqueous sodium hydroxide solution (8.06 mL), and tetrahydrofuran (10.0 mL) was added acetic anhydride (0.457 mL), followed by stirring at room temperature for 3 hours. The mixture was adjusted to be weakly acidic by the addition of 1 M hydrochloric acid. This mixture was extracted with ethyl acetate, and the organic layer was washed with saturated brine and then dried over anhydrous sodium sulfate. The insoluble materials were separated by filtration and the filtrate was concentrated under reduced pressure to obtain 3-(1-acetamidepropan-2-yl)-5-methoxy-1H-indole-2-carboxylic acid (1.16 g) as a brown amorphous substance.

Preparation Example 31

To a mixture of 3-(1-aminopropan-2-yl)-5-methoxy-1H-indole-2-carboxylic acid (1.00 g) and tetrahydrofuran (10.0 mL) was added 4-nitrophenyl 1-methylcarbamate (790 mg), followed by stirring at 60° C. for 3 hours. To the mixture was added a 1 M aqueous sodium hydroxide solution (5.00 mL), followed by stirring for 1 hour. The mixture was neutralized by the addition of 1 M hydrochloric acid, followed by extraction with ethyl acetate. The organic layer was washed with saturated brine and then dried over anhydrous sodium sulfate. The insoluble materials were separated by filtration and the filtrate was concentrated under reduced pressure to obtain 5-methoxy-3-{1-[(methylcarbamoyl)amino]propan-2-yl}-1H-indole-2-carboxylic acid (1.23 g) as a brown viscous oily substance.

Preparation Example 32

A mixture of 3-[(7-chloro-2,3-dihydro-1-benzofuran-5-yl) hydrazinylidene]piperidin-2-one (a mixture of E and Z isomers) (3.66 g) and formic acid (65.4 mL) was stirred at 100° C. for 1 hour. After cooling to room temperature, the reaction mixture was concentrated under reduced pressure and the obtained residue was purified by silica gel column chromatography (chloroform:methanol=100:0 to 95:5) to obtain an orange solid. This solid was washed with ethyl acetate to obtain a mixture (1.74 g) of 4-chloro-1,2,6,8,9,10-hexahydro-7H-furo[3,2-e]pyrido[3,4-b]indol-7-one and 10-chloro-2,3,5,7,8,9-hexahydro-6H-furo[2,3-f]pyrido[3,4-b]indol-6-one as an orange solid.

Preparation Example 33

To a mixture of 3-(2-aminoethyl)-6-fluoro-5-methoxy-1H-indole-2-carboxylic acid (1.90 g) and tetrahydrofuran (38.0 mL) were added diisopropylethylamine (6.45 mL) and acetic anhydride (1.42 mL), followed by stirring at room temperature overnight. To the reaction mixture was added a 1 M aqueous sodium hydroxide solution (50.0 mL), followed by stirring for 1 hour and acidifying by the addition of 1 M hydrochloric acid (90.0 mL). This mixture was extracted with ethyl acetate, and the organic layer was washed with saturated brine and then dried over anhydrous sodium sulfate. The insoluble materials were separated by filtration and the filtrate was concentrated under reduced pressure to obtain 3-(2-acetamidoethyl)-6-fluoro-5-methoxy-1H-indole-2-carboxylic acid (2.21 g) as a pale yellow solid.

Preparation Examples 34 to 66

In the same manner as the methods of Preparation Examples 1 to 33, the compounds shown in Preparation Example Nos. (PEx) 34 to 66 in Tables below were prepared. The preparation methods, structures, and the physicochemical data of Preparation Example compounds are shown in Tables 6 to 15.

Example 1

To a mixture of 3-(2-acetamidoethyl)-5-methoxy-1H-indole-2-carboxylic acid (100 mg), diisopropylethylamine (0.310 mL), methylamine hydrochloride (73.3 mg), and N,N-dimethyl formamide (1.75 mL) was added 2-(7-aza-1H-benzotriazol-1-yl)-1,1,3,3-tetramethyluronium hexafluorophosphate (206 mg), followed by stirring at room temperature overnight. To the mixture was added ice water, followed by extraction with ethyl acetate, and the organic layer was washed with saturated brine and dried over anhydrous sodium sulfate. The insoluble materials were separated by filtration, the filtrate was concentrated under reduced pressure, and then the obtained residue was purified by silica gel column chromatography (chloroform:methanol=100:0 to 20:1) to obtain 3-(2-acetamidoethyl)-5-methoxy-N-methyl-1H-indole-2-carboxamide (80.0 mg) as a white solid.

Example 2

To a mixture of 3-(2-aminoethyl)-5-methoxy-N-methyl-1H-indole-2-carboxamide hydrochloride (90.0 mg) and dichloromethane (5.00 mL) were added diisopropylethylamine (0.163 mL) and difluoroacetic anhydride (0.0470 mL), followed by stirring at room temperature for 1 hour. The solvent was evaporated under reduced pressure and the residue was purified by silica gel column chromatography (chloroform:methanol=10:0 to 10:1). The obtained residue was solidified with a mixed solvent of hexane:ethyl acetate=2:1 to obtain 3-{2-[(difluoroacetyl)amino]ethyl}-5-methoxy-N-methyl-1H-indole-2-carboxamide (73.0 mg) as a white solid.

Example 3

To a mixture of 3-(2-aminoethyl)-5-methoxy-N-methyl-1H-indole-2-carboxamide hydrochloride (80.0 mg) and dichloromethane (4.44 mL) were added diisopropylethylamine (0.145 mL) and propionyl chloride (0.0296 mL), followed by stirring at room temperature for 1 hour. The reaction mixture was concentrated under reduced pressure and the residue was purified by silica gel column chromatography (chloroform:methanol=10:0 to 10:1). The obtained residue was solidified with a mixed solvent of hexane:ethyl acetate=2:1 to obtain 5-methoxy-N-methyl-3-[2-(propionylamino)ethyl]-1H-indole-2-carboxamide (56.0 mg) as a white solid.

Example 4

To a mixture of 3-(2-aminoethyl)-5-methoxy-N-methyl-1H-indole-2-carboxamide hydrochloride (90.0 mg) and acetonitrile (5.00 mL) were added 2-fluoropropionic acid (0.0495 mL), diisopropylethylamine (0.272 mL), and 2-(7-aza-1H-benzotriazol-1-yl)-1,1,3,3-tetramethyluronium hexafluorophosphate (181 mg), followed by stirring at room temperature overnight. The reaction mixture was concentrated under reduced pressure and the obtained residue was purified by silica gel column chromatography (chloroform:methanol=10:0 to 10:1). The obtained residue was solidified with a mixed solvent of hexane:ethyl acetate=2:1 to obtain 3-{2-[(2-fluoropropanoyl)amino]ethyl}-5-methoxy-N-methyl-1H-indole-2-carboxamide (70.0 mg) as a white solid.

Example 5

To a mixture of 3-{2-[(difluoroacetyl)amino]ethyl}-5-hydroxy-N-methyl-1H-indole-2-carboxamide (102 mg) and N,N-dimethyl formamide (3.00 mL) were added potassium carbonate (55.2 mg) and ethyl iodide (0.0318 mL), followed by stirring at room temperature for 2 hours, then warming to 60° C., and stirring overnight. To this mixture was added water, followed by extraction with ethyl acetate, and the organic layer was washed with saturated brine and subsequently dried over anhydrous sodium sulfate. The insoluble materials were separated by filtration, the filtrate was concentrated under reduced pressure, and then the obtained residue was purified by silica gel chromatography (chloroform:methanol=100:0 to 94:6) to obtain a colorless solid. The obtained solid was washed with hexane:ethyl acetate=2:1 to obtain 3-{2-[(difluoroacetyl)amino]ethyl}-5-ethoxy-N-methyl-1H-indole-2-carboxamide (9.00 mg) as a colorless solid.

Example 6

To a mixture of 3-{2-[(difluoroacetyl)amino]ethyl}-5-hydroxy-N-methyl-1H-indole-2-carboxamide (103 mg), chloroacetonitrile (0.0313 mL), and acetonitrile (3.00 mL) were added cesium carbonate (377 mg) and tetrabutylammonium iodide (24.4 mg), followed by stirring at 60° C. for 3 hours. To the mixture was added chloroacetonitrile (0.0209 mL), followed by stirring at 60° C. for 1 hour. To this mixture was added water, followed by extraction with ethyl acetate, the organic layer was washed with saturated brine and subsequently dried over anhydrous sodium sulfate. The insoluble materials were separated by filtration, the filtrate was concentrated under reduced pressure, and then the obtained residue was purified by silica gel column chromatography (chloroform:methanol=100:0 to 94:6) to obtain a pale yellow solid. The obtained solid was washed with hexane:ethyl acetate=2:1 to obtain 5-(cyanomethoxy)-3-{2-[(difluoroacetyl)amino]ethyl}-N-methyl-1H-indole-2-carboxamide (5.00 mg) as a pale yellow solid.

Example 7

To a mixture of 3-(2-acetamidoethyl)-6-fluoro-5-methoxy-1H-indole-2-carboxylic acid (200 mg), ammonium chloride (110 mg), 1-hydroxybenzotriazole (140 mg), and acetonitrile (4.00 mL) were added triethylamine (0.300 mL) and 1-ethyl-3-(3-dimethylaminopropyl)carbodiimide hydrochloride (200 mg), followed by stirring at room temperature overnight. To the mixture was added an aqueous sodium hydrogen carbonate solution, followed by extraction with chloroform, and the organic layer was concentrated under reduced pressure. The obtained residue was purified by silica gel column chromatography (chloroform:methanol=96:4 to 9:1). To the obtained crude product was added ethyl acetate, followed by heating. Then, diisopropylether was added thereto, followed by stirring at room temperature. The resulting solid was collected by filtration and dried under reduced pressure to obtain 3-(2-acetamidoethyl-6-fluoro-5-methoxy-1H-indole-2-carboxamide (153 mg) as a white solid.

Example 8

To 3-(2-aminoethyl)-5-methoxy-N-methyl-1H-indole-2-carboxamide hydrochloride (167 mg) were added tetrahydrofuran (2.00 mL), triethylamine (0.246 mL), and 1,1'-carbonyldiimidazole (143 mg), followed by stirring at room temperature for 15 minutes. Then, methylamine (2 M tetrahydrofuran solution, 1.77 mL) was added thereto, followed by warming to 50° C. and stirring for 1 hour. The reaction mixture was cooled to room temperature, silica gel was added thereto, and the solvent was evaporated under reduced pressure. The obtained residue was purified by silica gel column chromatography (chloroform:methanol=100:0 to 20:1) to obtain 5-methoxy-N-methyl-3-{2-[(methylcarbamoyl)amino]ethyl}-1H-indole-2-carboxamide (144 mg) as a white solid.

Example 9

To 3-(2-aminoethyl)-5-methoxy-N-methyl-1H-indole-2-carboxamide hydrochloride (100 mg) were added tetrahydrofuran (1.20 mL), triethylamine (0.147 mL), and ethylisocyanate (0.0415 mL), followed by stirring for 1 hour. To the mixture were added silica gel and methanol, and the solvent was evaporated under reduced pressure. The obtained residue was purified by silica gel column chromatography (chloroform:methanol=100:0 to 94:6) to obtain a colorless solid. The obtained solid was washed with hexane/ethyl acetate to obtain 3-{2-[(ethylcarbamoyl)amino]ethyl}-5-methoxy-N-methyl-1H-indole-2-carboxamide (86.0 mg) as a colorless solid.

Example 10

To a mixture of 3-(2-aminoethyl)-5-methoxy-N-methyl-1H-indole-2-carboxamide hydrochloride (116 mg), diisopropylethylamine (0.146 mL), and tetrahydrofuran (4.63 mL) was added 4-nitrophenyl 1-methoxycarbamate (90.9 mg), warming to 60° C. and stirring for 3.5 hours. To the mixture were added chloroform and a 1 M aqueous sodium hydroxide solution, followed by stirring, and the organic layer was separated using a phase separator (Biotage) and concentrated under reduced pressure. The obtained residue was purified by silica gel column chromatography (chloroform:methanol=50:1 to 10:1 amino silica gel). The obtained crude product was solidified with diisopropyl ether, and the obtained solid was collected by filtration and dried under reduced pressure to obtain 5-methoxy-3-{2-[(methoxycarbamoyl)amino]ethyl}-N-methyl-1H-indole-2-carboxamide (42.6 mg).

Example 11

To a mixture of 3-(2-aminoethyl)-5-methoxy-1H-pyrrolo[3,2-b]pyridine-2-carboxylic acid (123 mg) and tetrahydrofuran (2.00 mL) were added diisopropylethylamine (0.448 mL) and acetic anhydride (0.074 mL), followed by stirring at room temperature overnight. To the mixture was added a 1 M aqueous sodium hydroxide solution (3.00 mL), followed by stirring for 1 hour, and then 1 M hydrochloric acid (3.00 mL) was added thereto, followed by concentrating under reduced pressure. The residue was suspended in ethanol, the insoluble materials were separated by filtration, and then the filtrate was concentrated under reduced pressure. To a mixture of the obtained residue (144 mg), methylamine hydrochloride (175 mg), diisopropylethylamine (0.622 mL), and N,N-dimethyl formamide (4.65 mL) was added 2-(7-aza-1H-benzotriazol-1-yl)-1,1,3,3-tetramethyluronium hexafluorophosphate (592 mg), followed by stirring at room temperature overnight. To the mixture was added water, followed by extraction with ethyl acetate, and the organic layer was washed with saturated brine and then dried over anhydrous sodium sulfate. The insoluble materials were separated by filtration and the filtrate was concentrated under reduced pressure. The obtained residue was purified by silica gel column chromatography (chloroform:methanol=100:1 to 20:1) and the obtained crude product was solidified with diethyl ether and the obtained solid was collected by filtration and dried under reduced pressure to obtain 3-(2-acetamidoethyl)-5-methoxy-N-methyl-1H-pyrrolo[3,2-b]pyridine-2-carboxamide (81.0 mg) as a pale yellow solid.

Example 12

To a mixture of 3-{2-[(tert-butoxycarbonyl)amino]ethyl}-6-chloro-5-methoxy-1H-indole-2-carboxylic acid (300 mg), diisopropylethylamine (0.696 mL), methylamine hydrochloride (165 mg), and N,N-dimethyl formamide (11.8 mL) was added 2-(7-aza-1H-benzotriazol-1-yl)-1,1,3,3-tetramethyluronium hexafluorophosphate (464 mg), followed by stirring at room temperature overnight. To the mixture was added ice water, followed by extraction with ethyl acetate, and the organic layer was washed with saturated brine and dried over anhydrous sodium sulfate. The insoluble materials were separated by filtration, the filtrate was concentrated under reduced pressure, and the obtained residue was purified by silica gel column chromatography (chloroform:methanol=100:0 to 10:1) to obtain a white solid (190 mg). To a mixture of the obtained solid (190 mg) and dioxane (5.00 mL) was added hydrogen chloride (4 M dioxane solution, 5.00 mL), followed by stirring at room temperature overnight. The reaction mixture was concentrated under reduced pressure to obtain a yellow solid (158 mg). To a mixture of the obtained solid (47.0 mg) and dichloromethane (5.00 mL) were added diisopropylethylamine (0.126 mL) and acetic anhydride (0.016 mL), followed by stirring at room temperature for 1 hour. The solvent was evaporated under reduced pressure and the residue was purified by silica gel column chromatography (chloroform:methanol=10:0 to 10:1). The obtained residue was washed with diisopropyl ether:diethyl ether to obtain 3-(2-acetamidoethyl)-6-chloro-5-methoxy-N-methyl-1H-indole-2-carboxamide (33.0 mg) as a white solid.

Example 13

To a mixture of tert-butyl {2-[7-fluoro-5-methoxy-2-(methylcarbamoyl)-1H-indol-3-yl]ethyl}carbamate (185 mg)

and dioxane (4.87 mL) was added hydrogen chloride (4 M dioxane solution, 5.09 mL), followed by stirring at room temperature overnight. The reaction mixture was concentrated under reduced pressure to obtain a yellow solid (140 mg). To a mixture of the obtained solid (70.0 mg) and dichloromethane (5.00 mL) were added diisopropylethylamine (0.119 mL) and acetic anhydride (0.0329 mL), followed by stirring at room temperature for 1 hour. The solvent was evaporated under reduced pressure and the residue was purified by silica gel column chromatography (chloroform: methanol=10:0 to 10:1). The obtained residue was solidified with hexane:ethyl acetate=1:1 to obtain 3-(2-acetamidoethyl)-7-fluoro-5-methoxy-N-methyl-1H-indole-2-carboxamide (31.0 mg) as a white solid.

In the same manner as the methods of Examples 1 to 13, the compounds of Examples 14 to 29, 31 to 33, 35 to 37 and 39 to 55 shown in Tables below were prepared.

Example 30

To a mixture of tert-butyl [2-(2-carbamoyl-5-methoxy-1H-indol-3-yl)ethyl]carbamate (1.72 g) and dioxane (15.0 mL) was added hydrogen chloride (4 M dioxane solution, 15.0 mL), followed by stirring at room temperature for 3 hours. The precipitated solid was collected by filtration and dried under reduced pressure to obtain a yellow solid (1.15 g). To a mixture of the obtained yellow solid (100 mg) and dichloromethane (5.56 mL) were added diisopropylethylamine (0.190 mL) and butyryl chloride (0.0388 mL), followed by stirring at room temperature for 1 hour. The solvent was evaporated under reduced pressure and the residue was purified by silica gel column chromatography (chloroform: methanol=10:0 to 10:1). The obtained residue was solidified with hexane:ethyl acetate=2:1 to obtain 3-[2-(butyrylamino)ethyl]-5-methoxy-1H-indole-2-carboxamide (77.0 mg) as a white solid.

Example 34

To a mixture of 3-{2-[(tert-butoxycarbonyl)amino]ethyl}-6-chloro-5-methoxy-1H-indole-2-carboxylic acid (300 mg), diisopropylethylamine (0.696 mL), methylamine hydrochloride (165 mg), and N,N-dimethyl formamide (11.8 mL) was added 2-(7-aza-1H-benzotriazol-1-yl)-1,1,3,3-tetramethyluronium hexafluorophosphate (464 mg), followed by stirring at room temperature overnight. To the mixture was added ice water, followed by extraction with ethyl acetate, and the organic layer was washed with saturated brine and dried over anhydrous sodium sulfate. The insoluble materials were separated by filtration, the filtrate was concentrated under reduced pressure, and the obtained residue was purified by silica gel column chromatography (chloroform:methanol=100:0 to 10:1) to obtain a white solid (190 mg). To a mixture of the obtained white solid (190 mg) and dioxane (5.00 mL) was added hydrogen chloride (4 M dioxane solution, 5.00 mL), followed by stirring at room temperature overnight, and the reaction mixture was concentrated under reduced pressure to obtain a residue (158 mg). To a mixture of the obtained residue (43.0 mg) and dichloromethane (2.69 mL) were added diisopropylethylamine (0.116 mL) and butyryl chloride (0.021 mL), followed by stirring at room temperature for 1 hour. The solvent was evaporated under reduced pressure and the residue was purified by silica gel column chromatography (chloroform:methanol=10:0 to 10:1). The obtained residue was washed with diisopropyl ether:diethyl ether to obtain 3-[2-(butyrylamino)ethyl]-6-chloro-5-methoxy-N-methyl-1H-indole-2-carboxamide (35.0 mg) as a white solid.

Example 38

To a mixture of tert-butyl [2-(2-carbamoyl-5-methoxy-1H-indol-3-yl)ethyl]carbamate (1.72 g) and dioxane (15.0 mL) was added hydrogen chloride (4 M dioxane solution, 15.0 mL), followed by stirring at room temperature for 3 hours. The precipitated solid was collected by filtration and dried under reduced pressure to obtain a yellow solid (1.15 g). To a mixture of the obtained yellow solid (100 mg) and diisopropylethylamine (0.317 mL), 3,3,3-trifluoropropionic acid (0.065 mL), and acetonitrile (5.00 mL) was added 2-(7-aza-1H-benzotriazol-1-yl)-1,1,3,3-tetramethyluronium hexafluorophosphate (211 mg), followed by stirring at room temperature overnight. The reaction mixture was concentrated under reduced pressure and the obtained residue was purified by silica gel column chromatography (chloroform: methanol=100:0 to 10:1) to obtain 5-methoxy-3-{2-[(3,3,3-trifluoropropanoyl)amino]ethyl}-1H-indole-2-carboxamide (90.0 mg).

Example 56

To a mixture of 3-(2-acetamidoethyl)-6-fluoro-5-methoxy-1H-indole-2-carboxylic acid (2.11 g), diisopropylethylamine (6.14 mL), methylamine hydrochloride (1.45 g), and N,N-dimethyl formamide (42.2 mL) was added 2-(7-aza-1H-benzotriazol-1-yl)-1,1,3,3-tetramethyluronium hexafluorophosphate (6.82 g), followed by stirring at room temperature overnight. To the mixture was added ice water, followed by extraction with ethyl acetate and further extraction with chloroform/methanol (10:1). The organic layer was washed with saturated brine and dried over anhydrous sodium sulfate. The insoluble materials were separated by filtration, the filtrate was concentrated under reduced pressure, and then the obtained residue was purified by silica gel column chromatography (chloroform:methanol=100:0 to 10:1) to obtain 3-(2-acetamidoethyl)-6-fluoro-5-methoxy-N-methyl-1H-indole-2-carboxamide (1.64 g).

The previously obtained 3-(2-acetamidoethyl)-6-fluoro-5-methoxy-N-methyl-1H-indole-2-carboxamide (1.46 g) was dissolved in warmed ethanol (18 mL), cooled to room temperature, and then stirred at room temperature for 3 days. The precipitated solid was collected by filtration and dried at 50° C. overnight under reduced pressure to obtain 3-(2-acetamidoethyl)-6-fluoro-5-methoxy-N-methyl-1H-indole-2-carboxamide (1.00 g) as a colorless crystal.

Example 57

To a mixture of 3-{2-[(difluoroacetyl)amino]ethyl}-6-fluoro-5-methoxy-1H-indole-2-carboxylic acid (2.48 g), methylamine hydrochloride (2.54 g), diisopropylethylamine (9.00 mL), and N,N-dimethyl formamide (49.6 mL) was added 2-(7-aza-1H-benzotriazol-1-yl)-1,1,3,3-tetramethyluronium hexafluorophosphate (8.57 g), followed by stirring at room temperature for 1 hour. To the mixture was added ice water, followed by extraction with ethyl acetate and further extraction with chloroform/methanol (10:1). The organic layer was washed with saturated brine and dried over anhydrous sodium sulfate. The insoluble materials were separated by filtration, the filtrate was concentrated under reduced pressure, and then the obtained residue was purified by silica gel column chromatography (chloroform:methanol=100:0 to 10:1) to obtain 3-{2-[(difluoroacetyl)amino]ethyl}-6-fluoro-5-methoxy-N-methyl-1H-indole-2-carboxamide (1.42 g).

The previously obtained 3-{2-[(difluoroacetyl)amino]ethyl}-6-fluoro-5-methoxy-N-methyl-1H-indole-2-carboxamide (1.24 g) was dissolved in warmed ethanol (23 mL), cooled to room temperature, and then stirred at room temperature for 3 days. The precipitated solid was collected by filtration and dried at 50° C. overnight under reduced pressure to obtain 3-{2-[(difluoroacetyl)amino]ethyl}-6-fluoro-5-methoxy-N-methyl-1H-indole-2-carboxamide (932 mg).

The structures of Example compounds are shown in Tables 16 to 25, and the physicochemical data and the preparation methods are shown in Tables 26 to 29, respectively.

TABLE 6

| PEx | PSyn | Str | DATA |
|-----|------|-----|------|
| 1 | 1 | | ESI+: 293 |
| 2 | 2 | | ESI+: 305 |
| 3 | 3 | | ESI+: 277 |
| 4 | 4 | | ESI+: 363 |
| 5 | 5 | | ESI+: 348 |

TABLE 6-continued

| PEx | PSyn | Str | DATA |
|-----|------|-----|------|
| 6 | 6 | | ESI+: 248 |

TABLE 7

| PEx | PSyn | Str | DATA |
|-----|------|-----|------|
| 7 | 7 | | APCI/ESI+: 312 |
| 8 | 8 | | ESI+: 252 |
| 9 | 9 | | ESI+: 235 |
| 10 | 10 | | ESI+: 253 |
| 11 | 11 | | APCI/ESI+: 331 |

TABLE 7-continued

| PEx | PSyn | Str | DATA |
|---|---|---|---|
| 12 | 12 | [structure: 5-methoxy-6-chloro-3-(2-(Boc-amino)ethyl)-1H-indole-2-carboxylic acid] | ESI+: 369, 371 |
| 13 | 13 | [structure: 2-allyl-6-chloro-4-nitrophenol] | ESI+: 214 |

TABLE 8

| PEx | PSyn | Str | DATA |
|---|---|---|---|
| 14 | 14 | [structure: 3-(3-chloro-5-nitro-2-hydroxyphenyl)propane-1,2-diol] | ESI−: 246 |
| 15 | 15 | [structure: 2-(2-hydroxyethyl)-6-chloro-4-nitrophenol] | APCI/ESI−: 216 |
| 16 | 16 | [structure: 7-chloro-5-nitro-2,3-dihydrobenzofuran] | EI: 199, 201 |
| 17 | 17 | [structure: 7-chloro-5-amino-2,3-dihydrobenzofuran] | ESI+: 170 |
| 18 | 18 | [structure: chloro-substituted dihydrofuro-indole-carboxylic acid with Boc-aminoethyl] and | APCI/ESI−: 379 |

TABLE 8-continued

| PEx | PSyn | Str | DATA |
|---|---|---|---|
| | | [structure: chloro-substituted dihydrofuro-indole-carboxylic acid with Boc-aminoethyl] | |

TABLE 9

| PEx | PSyn | Str | DATA |
|---|---|---|---|
| 19 | 19 | [structure: fluoro-substituted dihydrofuro-indole-carboxylic acid with Boc-aminoethyl and N-Boc] and | APCI/ESI−: 463 |
| | | [structure: fluoro-substituted dihydrofuro-indole-carboxylic acid with Boc-aminoethyl and N-Boc] | |
| 20 | 20 | [structure: dihydrofuro-indole-N-methylcarboxamide with Boc-aminoethyl] | APCI/ESI−: 358 |
| 21 | 21 | [structure: 5-(Boc-amino)-2,3-dihydrobenzofuran] | EI: 235 |
| 22 | 22 | [structure: 5-(Boc-amino)-6-bromo-2,3-dihydrobenzofuran] | ESI+: 314, 316 |
| 23 | 23 | [structure: 5-amino-6-bromo-2,3-dihydrobenzofuran HCl] | ESI+: 214, 216 |

TABLE 9-continued

| PEx | PSyn | Str | DATA |
|---|---|---|---|
| 24 | 24 | | EI: 306, 308 |
| 25 | 25 | | ESI+: 425, 427 |

TABLE 10

| PEx | PSyn | Str | DATA |
|---|---|---|---|
| 26 | 26 | | APCI/ESI−: 392 |
| 27 | 27 | | ESI+: 295, 297 |
| 28 | 28 | | ESI+: 366 |
| 29 | 29 | | ESI+: 371 |

TABLE 10-continued

| PEx | PSyn | Str | DATA |
|---|---|---|---|
| 30 | 30 | | ESI+: 291 |
| 31 | 31 | | ESI+: 306 |

TABLE 11

| PEx | PSyn | Str | DATA |
|---|---|---|---|
| 32 | 32 | and | APCI/ESI+: 263 |
| 33 | 33 | | ESI+: 295 |
| 34 | 3 | | ESI+: 335 |

TABLE 11-continued

| PEx | PSyn | Str | DATA |
|---|---|---|---|
| 35 | 5 | [structure: 4,6-difluoro-5-methoxy-3-(2-(Boc-amino)ethyl)-1H-indole-2-carboxylic acid N-methylamide] | ESI+: 384 |
| 36 | 5 | [structure: bromo-dihydrofuro-fused indole with 3-(2-(Boc-amino)ethyl) and N-methylcarboxamide] | APCI/ESI−: 436, 438 |
| 37 | 5 | [structure: 5-methoxy-3-(2-(Boc-amino)ethyl)-1H-indole-2-carboxylic acid N-ethylamide] | ESI+: 362 |

TABLE 12

| PEx | PSyn | Str | DATA |
|---|---|---|---|
| 38 | 5 | [structure: 5-methoxy-3-(2-(Boc-amino)ethyl)-1H-indole-2-carboxylic acid N,N-dimethylamide] | ESI+: 362 |
| 39 | 5 | [structure: 5-methoxy-3-(2-(Boc-amino)ethyl)-1H-indole-2-carboxamide] | ESI−: 332 |
| 40 | 6 | [structure: 4,6-difluoro-5-methoxy-3-(2-aminoethyl)-1H-indole-2-carboxylic acid N-methylamide HCl] | ESI+: 284 |

TABLE 12-continued

| PEx | PSyn | Str | DATA |
|---|---|---|---|
| 41 | 6 | [structure: dihydrofuro-fused indole with 3-(2-aminoethyl) and N-methylcarboxamide, HCl] | APCI/ESI+: 260 |
| 42 | 6 | [structure: chloro-dihydrofuro-fused indole with 3-(2-aminoethyl) and N-methylcarboxamide, HCl] | APCI/ESI+: 294 |
| 43 | 6 | [structure: fluoro-dihydrofuro-fused indole with 3-(2-aminoethyl) and N-methylcarboxamide, HCl] | ESI+: 278 |
| 44 | 6 | [structure: dihydrofuro-fused indole isomer with 3-(2-aminoethyl) and N-methylcarboxamide, HCl] | APCI/ESI+: 260 |

TABLE 13

| PEx | PSyn | Str | DATA |
|---|---|---|---|
| 45 | 8 | [structures: 3-chloro-4-methoxyphenyl hydrazone of 2-oxopiperidin-3-one (two tautomers shown) and] | ESI−: 266, 268 |
| 46 | 8 | [structure: 6-methoxypyridin-3-yl hydrazone of 2-oxopiperidin-3-one or] | ESI+: 235 |

TABLE 13-continued

| PEx | PSyn | Str | DATA |
|---|---|---|---|
| | | (MeO-pyridine-NHN=piperidinone) | |
| 47 | 8 | (dihydrobenzofuran-Cl, NHN=piperidinone) and (dihydrobenzofuran-Cl isomer) | APCI/ESI+: 280 |
| 48 | 8 | (dihydrobenzofuran-F, NHN=piperidinone) or (dihydrobenzofuran-F isomer) | ESI+: 264 |
| 49 | 8 | (dihydrobenzofuran-Br, NHN=piperidinone) and (dihydrobenzofuran-Br isomer) | APCI/ESI+: 324, 326 |

TABLE 13-continued

| PEx | PSyn | Str | DATA |
|---|---|---|---|
| 50 | 8 | (MeO-F-pyridine, NHN=piperidinone) or (MeO-F-pyridine isomer) | ESI+: 253 |
| 51 | 9 | (MeO-Cl tetrahydro-β-carbolinone) | ESI+: 251, 253 |

TABLE 14

| PEx | PSyn | Str | DATA |
|---|---|---|---|
| 52 | 9 | (MeO-pyrido-pyrrolo-pyridinone) | ESI+: 218 |
| 53 | 9 | (MeO-F-pyrido-pyrrolo-pyridinone) | ESI+: 236 |
| 54 | 10 | (MeO-Br-indole-ethylamine-carboxylic acid) | ESI−: 311, 313 |
| 55 | 10 | (MeO-azaindole-ethylamine-carboxylic acid) | ESI+: 236 |
| 56 | 10 | (MeO-diF-indole-ethylamine-carboxylic acid) | ESI+: 271 |

TABLE 14-continued
| PEx | PSyn | Str | DATA |
|---|---|---|---|
| 57 | 10 | 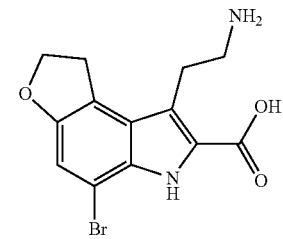 [SMILES: NCCc1c(C(=O)O)[nH]c2c(Br)cc3c(c12)CCO3] | ESI+: 325, 327 |
| 58 | 10 | | FAB+: 254 |
| 59 | 11 | | ESI+: 391, 393 |
TABLE 15
| PEx | PSyn | Str | DATA |
|---|---|---|---|
| 60 | 20 | 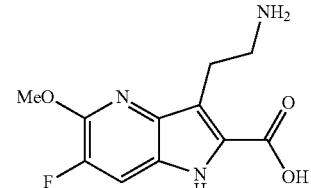 | APCI/ESI−: 358 |
| 61 | 26 | | APCI/ESI+: 478 |
| 62 | 32 | | APCI/ESI+: 247 |
TABLE 15-continued
| PEx | PSyn | Str | DATA |
|---|---|---|---|
| 63 | 5 | 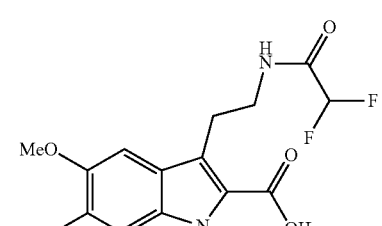 | ESI+: 366 |
| 64 | 6 | | ESI+: 266 |
| 65 | 25 | | ESI+: 353 |
| 66 | 26 | | APCI/ESI−: 392 |
TABLE 16
| Ex | Str |
|---|---|
| 1 | 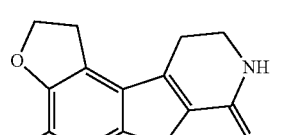 |
and TABLE 16-continued

| Ex | Str |
|---|---|
| 2 | (structure) |
| 3 | (structure) |
| 4 | (structure) |
| 5 | (structure) |
| 6 | (structure) |

TABLE 17

| Ex | Str |
|---|---|
| 7 | (structure) |
| 8 | (structure) |
| 9 | (structure) |
| 10 | (structure) |
| 11 | (structure) |
| 12 | (structure) |

TABLE 18

| Ex | Str |
|---|---|
| 13 | (structure) |
| 14 | (structure) |
| 15 | (structure) |
| 16 | (structure) |
| 17 | (structure) |
| 18 | (structure) |

TABLE 19

| Ex | Str |
|---|---|
| 19 | (structure) |
| 20 | (structure) |
| 21 | (structure) |
| 22 | (structure) |
| 23 | (structure) |
| 24 | (structure) |

TABLE 20
| Ex | Str |
|---|---|
| 25 | 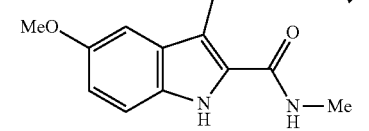 |
| 26 | |
| 27 | |
| 28 | |
| 29 | |
| 30 | |
TABLE 21
| Ex | Str |
|---|---|
| 31 | 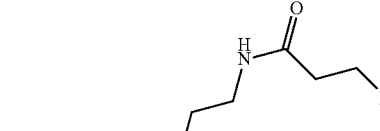 |
| 32 | |
| 33 | |
| 34 | |
| 35 | |
| 36 | |

TABLE 22

| Ex | Str |
|---|---|
| 37 | |
| 38 | |
| 39 | |
| 40 | |
| 41 | |
| 42 | |

TABLE 23

| Ex | Str |
|---|---|
| 43 | |
| 44 | |
| 45 | |
| 46 | |
| 47 | |
| 48 | |

TABLE 24

| Ex | Str |
|---|---|
| 49 | 5-methoxy-3-(2-(2,2-difluoroacetamido)ethyl)-1H-pyrrolo[3,2-b]pyridine-2-carboxamide |
| 50 | 3-(2-acetamidoethyl)-6-fluoro-5-methoxy-N-methyl-1H-pyrrolo[3,2-b]pyridine-2-carboxamide |
| 51 | 3-(2-(2,2-difluoroacetamido)ethyl)-6-fluoro-5-methoxy-N-methyl-1H-pyrrolo[3,2-b]pyridine-2-carboxamide |
| 52 | 6-chloro-3-(2-(2,2-difluoroacetamido)ethyl)-5-methoxy-N-methyl-1H-indole-2-carboxamide |
| 53 | 3-(2-(2,2-difluoroacetamido)ethyl)-7-fluoro-5-methoxy-N-methyl-1H-indole-2-carboxamide |
| 54 | 3-(2-(2,2-difluoroacetamido)ethyl)-N-ethyl-5-methoxy-1H-indole-2-carboxamide |

TABLE 25

| Ex | Str |
|---|---|
| 55 | 3-(2-(2,2-difluoroacetamido)ethyl)-5-methoxy-N,N-dimethyl-1H-indole-2-carboxamide |
| 56 | 3-(2-acetamidoethyl)-6-fluoro-5-methoxy-N-methyl-1H-indole-2-carboxamide |
| 57 | 3-(2-(2,2-difluoroacetamido)ethyl)-6-fluoro-5-methoxy-N-methyl-1H-indole-2-carboxamide |

TABLE 26

| Ex | Syn | DATA |
|---|---|---|
| 1 | 1 | ESI+: 290<br>1H-NMR(DMSO-d6)δ:<br>1.79 (3H, s), 2.83 (3H, d, J = 4.5 Hz), 3.07-3.24 (4H, m), 3.77 (3H, s), 6.85 (1H, dd, J = 2.4, 8.8 Hz), 7.09 (1H, d, J = 2.4 Hz), 7.28 (1H, d, J = 8.8 Hz), 7.93-7.98 (1H, m), 8.12-8.17 (1H, m), 11.03 (1H, s) |
| 2 | 2 | ESI+: 326<br>1H-NMR(DMSO-d6)δ:<br>2.82 (3H, d, J = 4.6 Hz), 3.18 (2H, t, J = 7.2 Hz), 3.35-3.39 (2H, m), 3.78 (3H, s), 6.14 (1H, t, J = 53.8 Hz), 6.86 (1H, dd, J = 2.4, 8.8 Hz), 7.11 (1H, d, J = 2.3 Hz), 7.29 (1H, d, J = 8.8 Hz), 7.93-7.97 (1H, m), 9.01-9.06 (1H, m), 11.05 (1H, s)<br>m.p.: 212-215° C. |
| 3 | 3 | ESI+: 304 |
| 4 | 4 | ESI+: 322 |
| 5 | 5 | ESI+: 340 |
| 6 | 6 | ESI+: 351 |
| 7 | 7 | ESI+: 294 |
| 8 | 8 | ESI+: 305<br>1H-NMR(DMSO-d6)δ:<br>2.57 (3H, d, J = 4.7 Hz), 2.85 (3H, d, J = 4.5 Hz), 3.03-3.09 (2H, m), 3.14-3.21 (2H, m), 3.77 (3H, s), 5.88 (1H, q, J = 4.7 Hz), 6.12 (1H, t, J = 5.1 Hz), 6.84 (1H, dd, J = 2.5, 8.8 Hz), 7.08 (1H, d, J = 2.5 Hz), 7.28 (1H, d, 8.8 Hz), 8.02 (1H, q, J = 4.5 Hz), 11.03 (1H, s) |
| 9 | 9 | ESI+: 319 |
| 10 | 10 | ESI+: 321 |
| 11 | 11 | ESI+: 291 |

TABLE 27

| Ex | Syn | DATA |
|---|---|---|
| 12 | 12 | ESI+: 324, 326<br>1H-NMR(DMSO-d6)δ:<br>1.78 (3H, s), 2.83 (3H, d, J = 4.5 Hz), 3.07-3.11 (2H, m), 3.20-3.25 (2H, m), 3.87 (3H, s), 7.29 (1H, s), 7.44 (1H, s), 7.99-8.14 (2H, m), 11.15 (1H, s) |
| 13 | 13 | ESI+: 308 |
| 14 | 1 | ESI+: 276 |
| 15 | 1 | ESI+: 344<br>1H-NMR(DMSO-d6)δ:<br>2.80 (3H, d, J = 4.5 Hz), 3.18 (2H, t, J = 7.0 Hz), 3.35-3.40 (2H, m), 3.85 (3H, s), 6.13 (1H, t, J = 53.7 Hz), 7.22 (1H, d, J = 11.5 Hz), 7.30 (1H, d, J = 8.5 Hz), 7.92-7.97 (1H, m), 8.99-9.03 (1H, m), 11.13 (1H, s) |
| 16 | 1 | ESI+: 330 |
| 17 | 1 | ESI+: 308<br>1H-NMR(DMSO-d6)δ:<br>1.79 (3H, s), 2.82 (3H, d, J = 4.5 Hz), 3.07-3.11 (2H, m), 3.19-3.25 (2H, m), 3.85 (3H, s), 7.20 (1H, d, J = 11.6 Hz), 7.29 (1H, d, J = 8.5 Hz), 7.93-7.98 (1H, m), 8.11-8.15 (1H, m), 11.12 (1H, s) |
| 18 | 1 | ESI+: 404, 406 |
| 19 | 1 | ESI+: 334 |
| 20 | 1 | ESI+: 304 |
| 21 | 1 | ESI+: 319 |
| 22 | 2 | ESI+: 344 |
| 23 | 13 | ESI+: 312 |
| 24 | 13 | ESI+: 290 |
| 25 | 2 | ESI+: 302 |
| 26 | 2 | ESI+: 336 |
| 27 | 2 | ESI+: 320 |
| 28 | 2 | ESI+: 302 |
| 29 | 2 | ESI+: 316 |
| 30 | 30 | ESI+: 304 |
| 31 | 3 | ESI+: 316 |
| 32 | 3 | ESI+: 318<br>1H-NMR(DMSO-d6)δ:<br>0.82 (3H, t, J = 7.4 Hz), 1.44-1.53 (2H, m), 2.01 (2H, t, J = 7.3 Hz), 2.83 (3H, d, J = 4.6 Hz), 3.07-3.11 (2H, m), 3.22-3.27 (2H, m), 3.78 (3H, s), 6.85 (1H, dd, J = 2.4, 8.9 Hz), 7.10 (1H, d, J = 2.4 Hz), 7.28 (1H, d, J = 8.9 Hz), 7.94-7.99 (1H, m), 8.05-8.08 (1H, m), 11.02 (1H, s) |
| 33 | 3 | ESI+: 320 |

TABLE 28

| Ex | Syn | DATA |
|---|---|---|
| 34 | 34 | ESI+: 352, 354<br>1H-NMR(DMSO-d6)δ:<br>0.80 (3H, t, J = 7.4 Hz), 1.43-1.52 (2H, m), 2.01 (2H, t, J = 7.4 Hz), 2.83 (3H, d, J = 4.6 Hz), 3.08-3.11 (2H, m), 3.22-3.27 (2H, m), 3.87 (3H, s), 7.29 (1H, s), 7.44 (1H, s), 8.02-8.07 (2H, m), 11.15 (1H, s) |
| 35 | 3 | ESI+: 336<br>1H-NMR(DMSO-d6)δ:<br>0.81 (3H, t, J = 7.4 Hz), 1.43-1.52 (2H, m), 2.01 (2H, t, J = 7.3 Hz), 2.83 (3H, d, J = 4.6 Hz), 3.08-3.12 (2H, m), 3.22-3.26 (2H, m), 3.86 (3H, s), 7.20 (1H, d, J = 11.6 Hz), 7.29 (1H, d, J = 8.5 Hz), 7.94-7.99 (1H, m), 8.04-8.07 (1H, m), 11.11 (1H, s) |
| 36 | 3 | ESI+: 322<br>1H-NMR(DMSO-d6)δ:<br>0.96 (3H, t, J = 7.7 Hz), 2.04 (2H, q, J = 7.7 Hz), 2.82 (3H, d, J = 4.5 Hz), 3.08-3.12 (2H, m), 3.21-3.26 (2H, m), 3.85 (3H, s), 7.19 (1H, d, J = 11.6 Hz), 7.28 (1H, d, J = 8.5 Hz), 7.93-8.05 (2H, m), 11.11 (1H, s) |
| 37 | 3 | ESI+: 326 |
| 38 | 38 | ESI+: 344 |
| 39 | 4 | ESI+: 358 |
| 40 | 4 | ESI+: 362 |
| 41 | 4 | ESI+: 338 |
| 42 | 4 | ESI+: 372 |
| 43 | 4 | ESI+: 356 |
| 44 | 4 | ESI+: 338 |
| 45 | 6 | ESI+: 376 |

TABLE 28-continued

| Ex | Syn | DATA |
|---|---|---|
| 46 | 8 | ESI+: 323 |
| 47 | 9 | ESI+: 337 |
| 48 | 11 | ESI+: 327<br>1H-NMR(CDCl3)δ:<br>3.10 (3H, d, J = 4.8 Hz), 3.32 (2H, t, J = 7.2 Hz), 3.66-3.71 (2H, m), 3.99 (3H, s), 5.88 (1H, t, J = 54 Hz), 6.73 (1H, d, J = 8.9 Hz), 6.85 (1H, brs), 7.42 (1H, brs), 7.62 (1H, d, J = 8.9 Hz), 9.08 (1H, brs) |
| 49 | 11 | ESI+: 313 |
| 50 | 11 | ESI+: 309 |
| 51 | 11 | ESI+: 345 |
| 52 | 12 | ESI+: 360, 362 |

TABLE 29

| Ex | Syn | DATA |
|---|---|---|
| 53 | 13 | ESI+: 344<br>1H-NMR(DMSO-d6)δ:<br>2.82 (3H, d, J = 4.6 Hz), 3.19 (2H, t, J = 7.0 Hz), 3.35-3.40 (2H, m), 3.79 (3H, s), 6.11 (1H, t, J = 53.8 Hz), 6.77 (1H, dd, J = 2.0, 12.5 Hz), 6.98 (1H, d, J = 2.0 Hz), 8.07-8.12 (1H, m), 8.95-8.99 (1H, m), 11.38 (1H, s) |
| 54 | 13 | ESI+: 340 |
| 55 | 13 | ESI+: 340 |
| 56 | 56 | ESI+: 308<br>1H-NMR(DMSO-d6)δ:<br>1.79 (3H, s), 2.83 (3H, d, J = 4.5 Hz), 3.06-3.14 (2H, m), 3.18-3.26 (2H, m), 3.85 (3H, s), 7.20 (1H, d, J = 11.6 Hz), 7.29 (1H, d, J = 8.5 Hz), 7.90-8.02 (1H, m), 8.08-8.18 (1H, m), 11.12 (1H, s)<br>m.p.: 209-212° C. |
| 57 | 57 | ESI+: 344<br>1H-NMR(DMSO-d6)δ:<br>2.81 (3H, d, J = 4.5 Hz), 3.18 (2H, t, J = 7.0 Hz), 3.33-3.42 (2H, m), 3.85 (3H, s), 6.13 (1H, t, J = 53.7 Hz), 7.22 (1H, d, J = 11.5 Hz), 7.30 (1H, d, J = 8.5 Hz), 7.88-8.00 (1H, m), 8.95-9.08 (1H, m), 11.13 (1H, s)<br>m.p.: 196-200° C. |

Moreover, the structures of other compounds of the compound of the formula (I) are shown in Tables 30 to 34. These can be easily prepared by any of the preparation methods above, the methods described in Examples, the methods apparent to those skilled in the art, or modified methods thereof.

TABLE 30

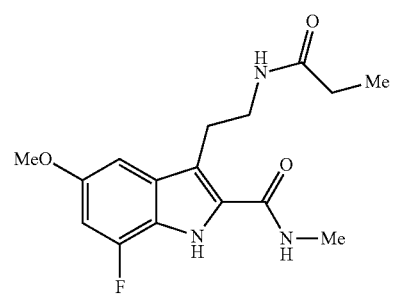 [SMILES: CCC(=O)NCCc1c(C(=O)NC)[nH]c2c(F)cc(OC)cc12]

TABLE 30-continued
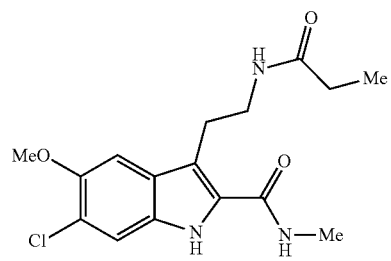 [SMILES: CCC(=O)NCCc1c(C(=O)NC)[nH]c2cc(Cl)c(OC)cc12]
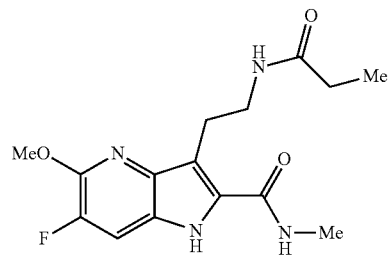 [SMILES: CCC(=O)NCCc1c(C(=O)NC)[nH]c2cc(F)c(OC)nc12]
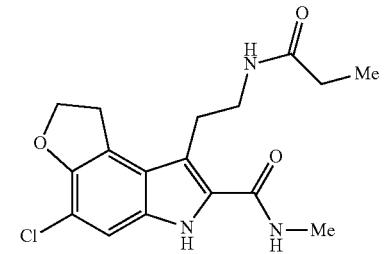 [SMILES: CCC(=O)NCCc1c(C(=O)NC)[nH]c2cc(Cl)c3c(c12)CCO3]
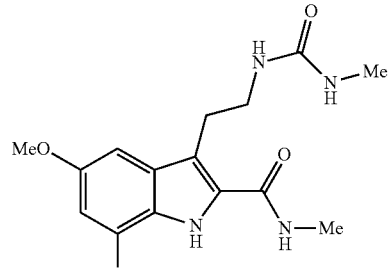
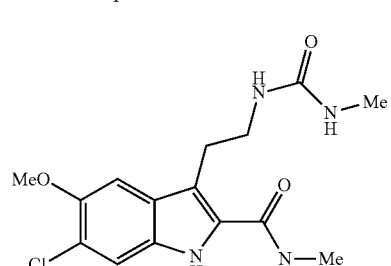
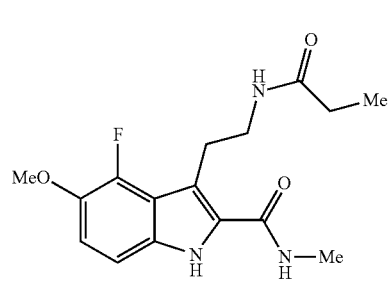 [SMILES: CCC(=O)NCCc1c(C(=O)NC)[nH]c2ccc(OC)c(F)c12]
TABLE 30-continued
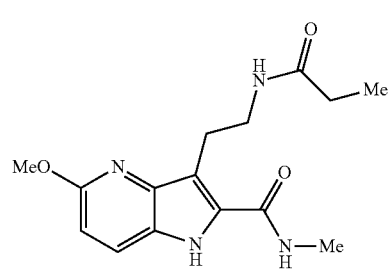 [SMILES: CCC(=O)NCCc1c(C(=O)NC)[nH]c2ccc(OC)nc12]
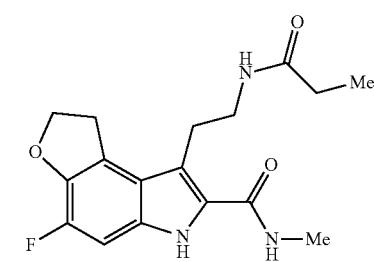 [SMILES: CCC(=O)NCCc1c(C(=O)NC)[nH]c2cc(F)c3c(c12)CCO3]
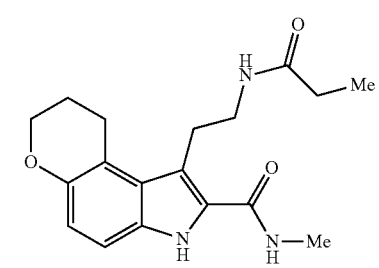 [SMILES: CCC(=O)NCCc1c(C(=O)NC)[nH]c2ccc3c(c12)CCCO3]
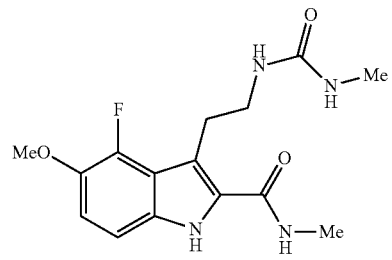 [SMILES: CNC(=O)NCCc1c(C(=O)NC)[nH]c2ccc(OC)c(F)c12]
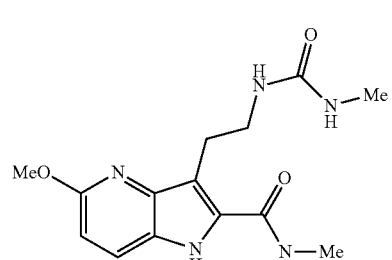

TABLE 31
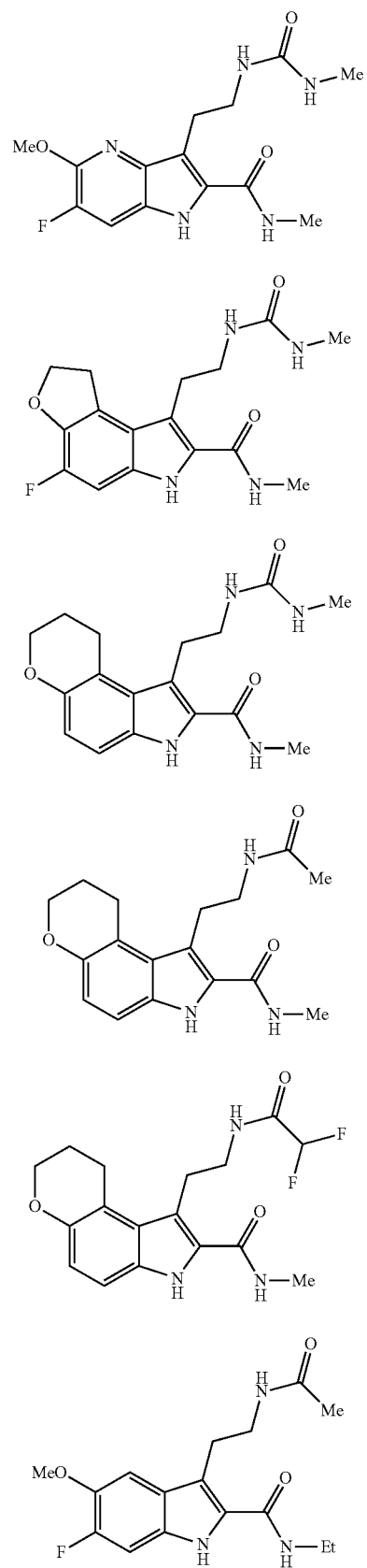
TABLE 31-continued
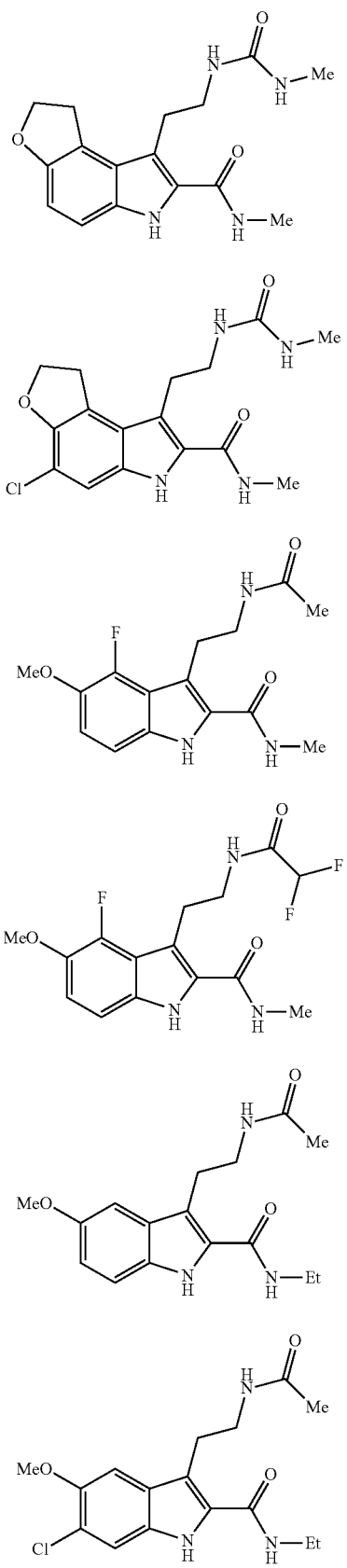

TABLE 32
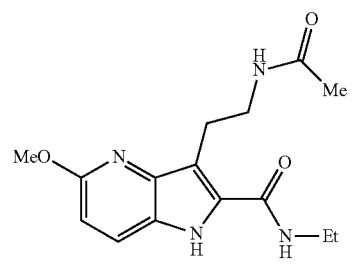
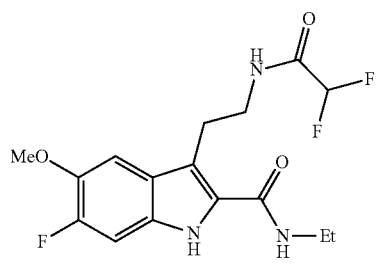
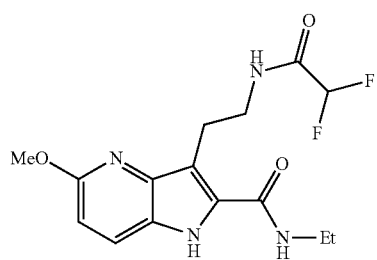 [SMILES: CCNC(=O)c1[nH]c2ccc(OC)nc2c1CCNC(=O)C(F)F]
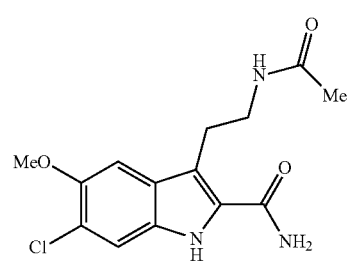
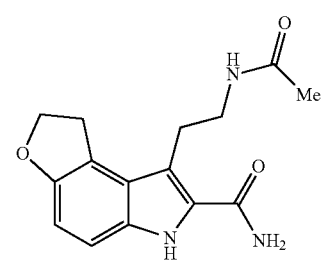 [SMILES: CC(=O)NCCc1c(C(N)=O)[nH]c2ccc3c(c12)CCO3]
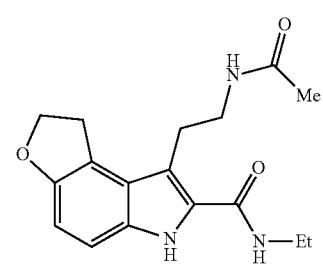 [SMILES: CCNC(=O)c1[nH]c2ccc3c(c2c1CCNC(C)=O)CCO3]
TABLE 32-continued
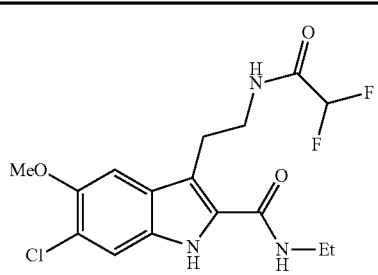
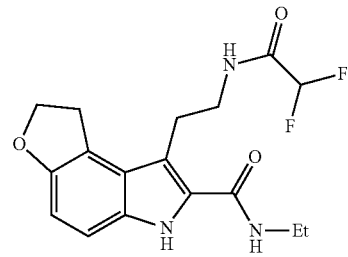 [SMILES: CCNC(=O)c1[nH]c2ccc3c(c2c1CCNC(=O)C(F)F)CCO3]
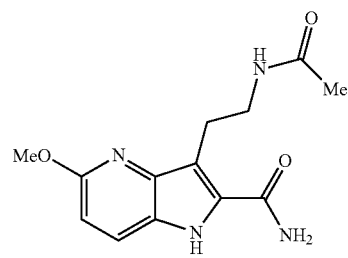 [SMILES: COc1ccc2[nH]c(C(N)=O)c(CCNC(C)=O)c2n1]
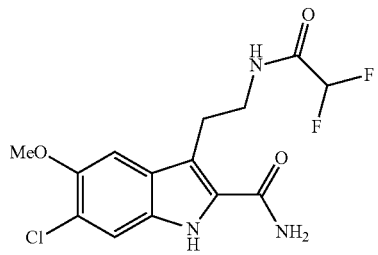 [SMILES: COc1cc2c(CCNC(=O)C(F)F)c(C(N)=O)[nH]c2cc1Cl]
TABLE 33
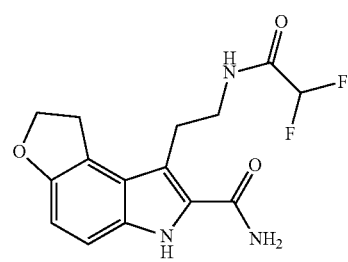 [SMILES: NC(=O)c1[nH]c2ccc3c(c2c1CCNC(=O)C(F)F)CCO3]

TABLE 33-continued
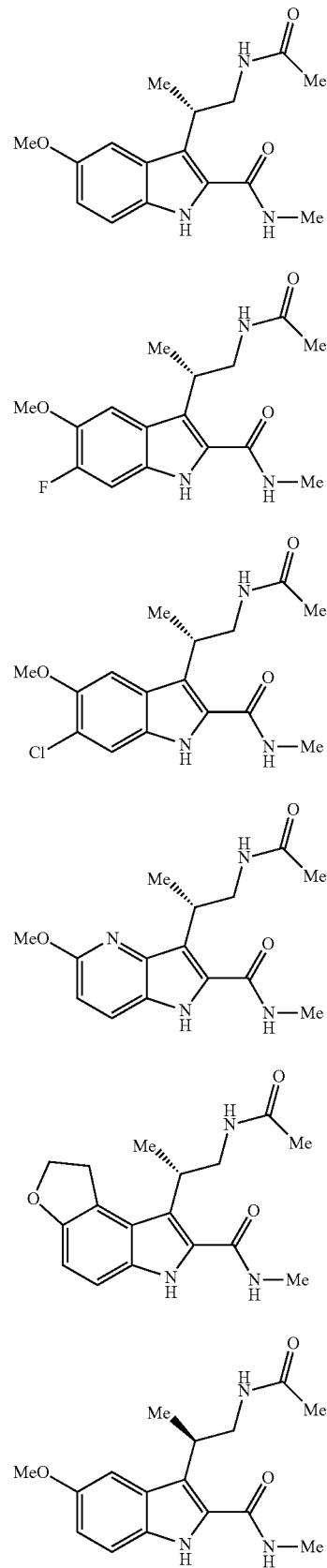
TABLE 33-continued
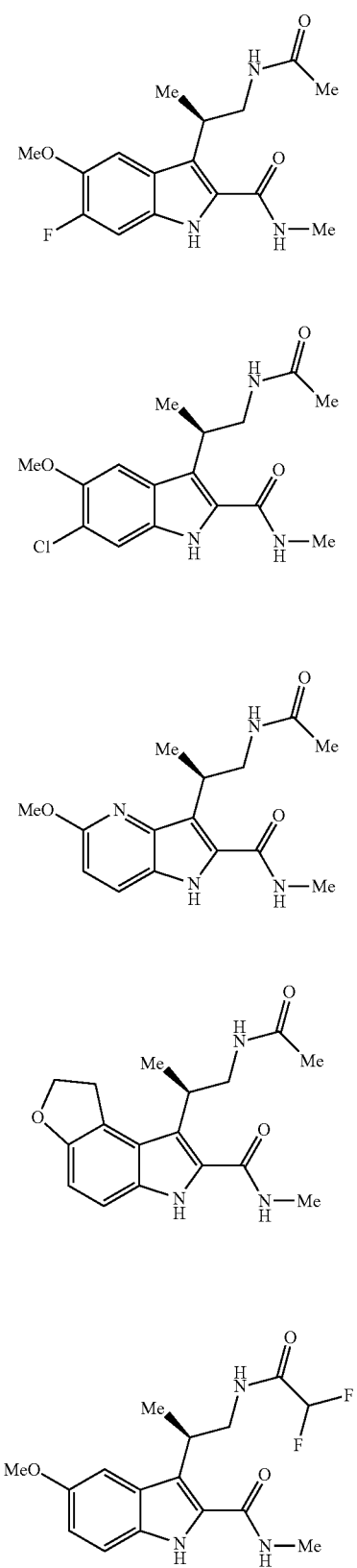

TABLE 34

TABLE 34-continued

INDUSTRIAL APPLICABILITY

The compound of the formula (I) or a salt thereof is a compound which acts as a peripheral MT1 and/or MT2 receptor agonist and does not exhibits a sleep action during administration of an effective dose in the application for treatment of urinary incontinence, and therefore, it is possible to separate the action on urinary incontinence and the action on the central nervous system disease. Thus, the compound of the formula (I) or a salt thereof can be used as an active ingredient for a pharmaceutical composition for preventing and/or treating urological diseases; in one embodiment, lower urinary tract symptoms; in another embodiment, urine storage symptom, in another embodiment, urinary incontinence; in a still another embodiment, stress urinary incontinence; and the like.

The invention claimed is:

1. A compound of the formula (I) or a salt thereof:

[Chem. 20]

(I)

wherein

Y is N or CR$^1$,

R$^1$, R$^3$, and R$^4$ are the same as or different from each other and are each H, halogen, or lower alkyl which may be substituted with one or more substituents selected from the group consisting of halogen, —OH, —O-lower alkyl, —O-halogeno-lower alkyl and —NR$^9$R$^{10}$, R$^2$ is lower alkyl which may be substituted with one or more substituents selected from the group consisting of halogen and cyano, and R$^2$ may be combined with R$^1$ to form —(CH$_2$)$_n$—, or R$^2$ may be combined with R$^3$ to form —(CH$_2$)$_n$—, n is 2 or 3, R$^{51}$ and R$^{52}$ are the same as or different from each other and are each H, lower alkyl which may be substituted with one or more substituents selected from Group G$^2$, or cycloalkyl which may be substituted with one or more substituents selected from Group G$^1$, and further, R$^{51}$ and R$^{52}$ may be combined with a nitrogen atom to which they are bonded to form cyclic amino which may be substituted with one or more substituents selected from Group G$^1$, X is a bond, —NR$^{11}$—, or —NR$^{11}$—O—, R$^{11}$ is H or lower alkyl, R$^6$ is lower alkyl which may be substituted with one or more substituents selected from Group G$^4$, or cycloalkyl which may be substituted with one or more substituents selected from Group G$^3$, further, when —X—R$^6$— is NR$^{11}$—R$^6$, R$^6$ and R$^{11}$ may be combined with a nitrogen atom to which they are bonded to form cyclic amino which may be substituted with one or more substituents selected from Group G$^3$, R$^7$ and R$^8$ are the same as or different from each other and are each H or lower alkyl which may be substituted with one or more substituents selected from the group consisting of halogen, —OH, and —O-halogeno-lower alkyl, Group G$^1$ and Group G$^3$ are lower alkyl, halogeno-lower alkyl, halogen, —OH, —O-lower alkyl, —O-halogeno-lower alkyl, and —NR$^9$R$^{10}$, Group G$^2$ and Group G$^4$ are halogen, —OH, —O-lower alkyl, —O-halogeno-lower alkyl, cycloalkyl which may be substituted with one or more halogen atoms, —O-(cycloalkyl which may be substituted with one or more halogen atoms), and —NR$^9$R$^{10}$, and R$^9$ and R$^{10}$ are the same as or different from each other and are H or lower alkyl).

2. The compound or a salt thereof according to claim 1, wherein

R$^1$ is H, halogen, or lower alkyl which may be substituted with one or more substituents selected from the group consisting of halogen, —O-lower alkyl, and —O-halogeno-lower alkyl, R$^3$ and R$^4$ are the same as or different from each other and are H, halogen, or lower alkyl which may be substituted with one or more substituents selected from the group consisting of halogen, —O-lower alkyl, and —O-halogeno-lower alkyl, R$^{51}$ and R$^{52}$ are the same as or different from each other and are each H, halogen, or lower alkyl which may be substituted with one or more substituents selected from Group G$^{21}$, cycloalkyl which may be substituted with one or more substituents selected from Group G$^{11}$, wherein Group G$^{11}$ is lower alkyl, halogeno-lower alkyl, halogen, —OH, and —O-lower alkyl, and Group G$^{21}$ is halogen, —OH, —O-lower alkyl, —O-halogeno-lower alkyl, and NR$^9$R$^{10}$, R$^6$ is lower alkyl which may be substituted with one or more substituents selected from Group G$^{41}$, or cycloalkyl which may be substituted with one or more substituents selected from Group G$^{31}$, wherein Group G$^{31}$ is lower alkyl, halogeno-lower alkyl, halogen, —OH, and —O-lower alkyl, and Group G$^{41}$ is halogen, —OH, —O-lower alkyl, —O-halogeno-lower alkyl, and cycloalkyl, and R$^7$ and R$^8$ are the same as or different from each other and are lower alkyl or H.

3. The compound or a salt thereof according to claim 2, wherein

R$^1$ is H or halogen,

R$^2$ is lower alkyl which may be substituted with one or more substituents selected from the group consisting of halogen and cyano, and further R$^2$ may be combined with R$^1$ to form —(CH$_2$)$_2$—, or R$^2$ may be combined with R$^3$ to form —(CH$_2$)$_2$, R$^3$ and R$^4$ are the same as or different from each other and are H or halogen, R$^{51}$ and R$^{52}$ are the same as or different from each other and are each H, lower alkyl, or cycloalkyl, X is a bond, —NH—, or —NH—O—, when X is a bond, R$^6$ is lower alkyl which may be substituted with one or more substituents selected from the group consisting of halogen and —O-lower alkyl, or cycloalkyl, or when X is —NH— or —NH—O—, R$^6$ is lower alkyl, and R$^7$ and R$^8$ are all H.

4. The compound or a salt thereof according to claim 3, wherein

R$^2$ is lower alkyl,

R$^{51}$ and R$^{52}$ are the same as or different from each other and are lower alkyl or H, and when X is a bond, R$^6$ is lower alkyl or halogeno-lower alkyl, or when X is —NH— or —NH—O—, R$^6$ is lower alkyl.

5. The compound or a salt thereof according to claim 4, wherein

R$^1$ is H or F,

R$^2$ is methyl,

R$^3$ and R$^4$ are the same as or different from each other and are H or F,

R$^{51}$ is methyl,

R$^{52}$ is H,

X is a bond or —NH—, and when X is a bond, R$^6$ is methyl or difluoromethyl, or when X is —NH—, R$^6$ is methyl.

6. The compound or a salt thereof according to claim 1, wherein Y is CR$^1$, R$^1$ is H, and X is a bond.

7. The compound or a salt thereof according to claim 1, wherein Y is CR$^1$, R$^1$ is H, and X is —NH—.

8. The compound or a salt thereof according to claim 1, wherein Y is N and X is a bond.

9. The compound or a salt thereof according to claim 1, wherein Y is N and X is —NH—.

10. The compound or a salt thereof according to claim 1, wherein the compound is selected from the group consisting of:

3-(2-acetamidoethyl)-5-methoxy-N-methyl-1H-indole-2-carboxamide,

3-{2-[(difluoroacetyl)amino]ethyl}-5-methoxy-N-methyl-1H-indole-2-carboxamide,

3-{2-[(difluoroacetyl)amino]ethyl}-6-fluoro-5-methoxy-N-methyl-1H-indole-2-carboxamide, 3-(2-acetamidoethyl)-6-fluoro-5-methoxy-N-methyl-1H-indole-2-carboxamide, and 5-methoxy-N-methyl-3-{2-[(methylcarbamoyl)amino]ethyl}-1H-indole-2-carboxamide.

11. A pharmaceutical composition comprising the compound or a salt thereof according to claim 1, and a pharmaceutically acceptable excipient.

12. The pharmaceutical composition according to claim 11, which is a pharmaceutical composition for preventing or treating urinary incontinence.

13. The pharmaceutical composition according to claim 12, wherein the compound has an action as a peripheral MT1 and/or MT2 receptor agonist.

14. The pharmaceutical composition according to claim 13, which does not exhibit a sleep action when administered in an effective dose.

15. The pharmaceutical composition according to claim 13, wherein the compound or salt thereof is selected from the group consisting of:
- 3-(2-acetamidoethyl)-5-methoxy-N-methyl-1H-indole-2-carboxamide,
- 3-{2-[(difluoroacetyl)amino]ethyl}-5-methoxy-N-methyl-1H-indole-2-carboxamide,
- 3-{2-[(difluoroacetyl)amino]ethyl}-6-fluoro-5-methoxy-N-methyl-1H-indole-2-carboxamide,
- 3-(2-acetamidoethyl)-6-fluoro-5-methoxy-N-methyl-1H-indole-2-carboxamide, and
- 5-methoxy-N-methyl-3-{2-[(methylcarbamoyl)amino]ethyl}-1H-indole-2-carboxamide.

16. A method for preventing or treating urinary incontinence, comprising administering to a subject an effective amount of the compound or a salt thereof according to claim 1.

17. The compound or a salt thereof according to claim 10, which is
3-(2-acetamidoethyl)-5-methoxy-N-methyl-1H-indole-2-carboxamide, or a salt thereof.

18. The compound or a salt thereof according to claim 10, which is
3-{2-[(difluoroacetyl)amino]ethyl}-5-methoxy-N-methyl-1H-indole-2-carboxamide, or a salt thereof.

19. The compound or a salt thereof according to claim 10, which is
3-{2-[(difluoroacetyl)amino]ethyl}-6-fluoro-5-methoxy-N-methyl-1H-indole-2-carboxamide, or a salt thereof.

20. The compound or a salt thereof according to claim 10, which is
3-(2-acetamidoethyl)-6-fluoro-5-methoxy-N-methyl-1H-indole-2-carboxamide, or a salt thereof.

21. The compound or a salt thereof according to claim 10, which is
5-methoxy-N-methyl-3-{2-[(methylcarbamoyl)amino]ethyl}-1H-indole-2-carboxamide, or a salt thereof.

* * * * *